United States Patent
Boardman et al.

(10) Patent No.: US 8,793,153 B2
(45) Date of Patent: Jul. 29, 2014

(54) SYSTEM AND METHOD FOR DETERMINING TRAILING DATA ADJUSTMENT FACTORS

(75) Inventors: Chris Boardman, Collegeville, PA (US); Brian Wynne, Wayne, PA (US); Kennon Copeland, Fredericksburg, VA (US)

(73) Assignee: IMS Software Services Ltd., Plymouth Meeting, PA (US)

( * ) Notice: Subject to any disclaimer, the term of this patent is extended or adjusted under 35 U.S.C. 154(b) by 508 days.

(21) Appl. No.: 12/421,566

(22) Filed: Apr. 9, 2009

(65) Prior Publication Data

US 2009/0281934 A1 Nov. 12, 2009

Related U.S. Application Data

(62) Division of application No. 11/293,592, filed on Dec. 2, 2005.

(60) Provisional application No. 60/646,791, filed on Jan. 25, 2005, provisional application No. 60/646,811, filed on Jan. 25, 2005, provisional application No. 60/646,812, filed on Jan. 25, 2005, provisional application No. 60/646,814, filed on Jan. 25, 2005, provisional application No. 60/646,815, filed on Jan. 25, 2005, provisional application No. 60/646,816, filed on Jan. 25, 2005.

(51) Int. Cl.
G06Q 10/00 (2012.01)
G06Q 30/00 (2012.01)

(52) U.S. Cl.
USPC ............................ 705/7.31; 705/2; 705/28

(58) Field of Classification Search
None
See application file for complete search history.

(56) References Cited

U.S. PATENT DOCUMENTS

| | | | |
|---|---|---|---|
| 4,355,372 A | | 10/1982 | Johnson et al. |
| 5,420,786 A | * | 5/1995 | Felthauser et al. ................ 705/2 |
| 5,459,656 A | | 10/1995 | Fields et al. |
| 5,596,493 A | | 1/1997 | Tone et al. |
| 5,704,044 A | | 12/1997 | Tarter et al. |
| 5,712,985 A | * | 1/1998 | Lee et al. ........................ 705/7 |
| 5,781,893 A | * | 7/1998 | Felthauser et al. ........... 705/7.34 |
| 5,854,746 A | | 12/1998 | Yamamoto et al. |
| 5,991,732 A | | 11/1999 | Moslares |
| 6,032,125 A | * | 2/2000 | Ando .......................... 705/7.31 |
| 6,249,774 B1 | | 6/2001 | Rodent et al. |

(Continued)

FOREIGN PATENT DOCUMENTS

| | | |
|---|---|---|
| EP | 1253544 | 10/2002 |
| EP | 1321883 | 6/2003 |
| WO | WO03/060642 | 7/2003 |
| WO | WO03/085488 | 10/2003 |

OTHER PUBLICATIONS

U.S. Appl. No. 12/421,561, Sep. 10, 2010 Notice of Allowance.
U.S. Appl. No. 12/421,532 (Abandoned), filed Apr. 9, 2009.

(Continued)

*Primary Examiner* — Ryan Zeender
*Assistant Examiner* — Dana Amsdell
(74) *Attorney, Agent, or Firm* — Fish & Richardson P.C.

(57) ABSTRACT

Timely projections of product sales for a reporting time period are obtained by combining actual sales data received from reporting stores and estimated sales data for non-reporting stores. The projections are adjusted to account for trailing data, which may be reported after the end of the subject time period.

16 Claims, 13 Drawing Sheets

(56) References Cited

U.S. PATENT DOCUMENTS

| | | | |
|---|---|---|---|
| 6,453,246 | B1 | 9/2002 | Agrafiotis et al. |
| 6,609,101 | B1 | 8/2003 | Landvater |
| 6,611,726 | B1 | 8/2003 | Crosswhite |
| 6,843,415 | B2 | 1/2005 | Vogler |
| 6,978,249 | B1 | 12/2005 | Beyer et al. |
| 7,069,233 | B2 | 6/2006 | Bracken et al. |
| 7,080,026 | B2 | 7/2006 | Singh et al. |
| 7,080,027 | B2 * | 7/2006 | Luby et al. .............. 705/7.31 |
| 7,092,929 | B1 * | 8/2006 | Dvorak et al. ............. 705/28 |
| 7,155,402 | B1 | 12/2006 | Dvorak |
| 7,174,304 | B1 | 2/2007 | Boardman |
| 7,314,170 | B2 | 1/2008 | Boardman et al. |
| 7,379,890 | B2 * | 5/2008 | Myr et al. .............. 705/7.35 |
| 7,480,623 | B1 | 1/2009 | Landvater |
| 7,552,066 | B1 | 6/2009 | Landvater |
| 7,580,851 | B1 | 8/2009 | Copeland |
| 7,813,953 | B2 | 10/2010 | Boardman et al. |
| 7,835,936 | B2 * | 11/2010 | Ouimet et al. ............ 705/7.31 |
| 7,844,479 | B2 | 11/2010 | Boardman et al. |
| 7,921,029 | B2 | 4/2011 | Boardman et al. |
| 8,078,488 | B2 | 12/2011 | Boardman et al. |
| 8,099,320 | B2 * | 1/2012 | Li et al. ................ 705/7.31 |
| 8,103,539 | B2 | 1/2012 | Boardman et al. |
| 8,452,635 | B2 * | 5/2013 | Caron et al. ............. 705/7.29 |
| 8,498,891 | B2 | 7/2013 | Boardman et al. |
| 2002/0143582 | A1 | 10/2002 | Neuman et al. |
| 2002/0147657 | A1 | 10/2002 | Callender et al. |
| 2002/0165762 | A1 | 11/2002 | Goldman et al. |
| 2002/0169652 | A1 | 11/2002 | Busche |
| 2002/0169657 | A1 | 11/2002 | Singh et al. |
| 2002/0169727 | A1 | 11/2002 | Melnick et al. |
| 2002/0184069 | A1 | 12/2002 | Kosiba et al. |
| 2003/0050799 | A1 | 3/2003 | Jay et al. |
| 2003/0050802 | A1 | 3/2003 | Jay et al. |
| 2003/0065555 | A1 * | 4/2003 | von Gonten et al. ......... 705/10 |
| 2003/0074250 | A1 | 4/2003 | Burk |
| 2003/0105773 | A1 | 6/2003 | Linde et al. |
| 2003/0110072 | A1 | 6/2003 | Delurgio et al. |
| 2003/0149581 | A1 | 8/2003 | Chaudhri et al. |
| 2003/0171950 | A1 | 9/2003 | Kilgannon et al. |
| 2003/0177055 | A1 * | 9/2003 | Zimmerman et al. ........ 705/10 |
| 2003/0177057 | A1 * | 9/2003 | Aronowich et al. ......... 705/10 |
| 2003/0204434 | A1 | 10/2003 | Linton et al. |
| 2003/0233246 | A1 | 12/2003 | Snapp et al. |
| 2004/0088211 | A1 | 5/2004 | Kakouros et al. |
| 2004/0122726 | A1 | 6/2004 | Linde et al. |
| 2004/0260599 | A1 | 12/2004 | Ziegele et al. |
| 2005/0055275 | A1 * | 3/2005 | Newman et al. ............ 705/14 |
| 2005/0273377 | A1 | 12/2005 | Ouimet et al. |
| 2006/0074695 | A1 | 4/2006 | Houson et al. |
| 2006/0111963 | A1 | 5/2006 | Li et al. |
| 2006/0178929 | A1 | 8/2006 | Boardman et al. |
| 2006/0178955 | A1 | 8/2006 | Boardman et al. |
| 2006/0190288 | A1 | 8/2006 | Boardman et al. |
| 2006/0190311 | A1 | 8/2006 | Boardman et al. |
| 2006/0206357 | A1 | 9/2006 | Boardman et al. |
| 2006/0206365 | A1 | 9/2006 | Boardman |
| 2008/0294996 | A1 | 11/2008 | Hunt et al. |
| 2009/0094056 | A1 | 4/2009 | Aeder et al. |
| 2009/0125385 | A1 | 5/2009 | Landvater |
| 2009/0132343 | A1 | 5/2009 | Boardman et al. |
| 2009/0259509 | A1 | 10/2009 | Landvater |
| 2009/0281828 | A1 | 11/2009 | Boardman et al. |
| 2009/0281934 | A1 | 11/2009 | Boardman et al. |
| 2009/0287538 | A1 | 11/2009 | Boardman et al. |
| 2009/0287539 | A1 | 11/2009 | Boardman et al. |
| 2009/0287540 | A1 | 11/2009 | Boardman et al. |
| 2009/0287541 | A1 | 11/2009 | Boardman et al. |
| 2009/0287542 | A1 | 11/2009 | Boardman et al. |
| 2009/0313066 | A1 | 12/2009 | Boardman et al. |
| 2010/0121675 | A1 | 5/2010 | Charles |

OTHER PUBLICATIONS

U.S. Appl. No. 12/421,552 (Abandoned), filed Apr. 9, 2009.
U.S. Appl. No. 12/421,507, May 5, 2011 Final Office Action.
U.S. Appl. No. 12/421,507, Mar. 9, 2011 Response to Non-Final Office Action.
U.S. Appl. No. 12/421,507, Sep. 9, 2010 Non-Final Office Action.
U.S. Appl. No. 11/293,602, Jun. 9, 2011 Final Office Action.
U.S. Appl. No. 11/293,602, Mar. 28, 2011 Response to Non-Final Office Action.
U.S. Appl. No. 11/293,602, Sep. 27, 2010 Non-Final Office Action.
U.S. Appl. No. 11/293,602, Aug. 18, 2010 Amendment and Request for Continued Examination (RCE).
U.S. Appl. No. 11/293,602, Mar. 19, 2010 Final Office Action.
U.S. Appl. No. 11/293,602, Nov. 16, 2009 Response to Non-Final Office Action.
U.S. Appl. No. 11/293,602, May 15, 2009 Non-Final Office Action.
U.S. Appl. No. 11/293,604, Nov. 29, 2010 Notice of Allowance.
U.S. Appl. No. 11/293,604, Sep. 13, 2010 Response to Non-Final Office Action.
U.S. Appl. No. 11/293,604, Jun. 14, 2010 Non-Final Office Action.
U.S. Appl. No. 11/293,604, Apr. 9, 2010 Amendment and Request for Continued Examination (RCE).
U.S. Appl. No. 11/293,604, Jan. 4, 2010 Final Office Action.
U.S. Appl. No. 11/293,604, Sep. 17, 2009 Response to Non-Final Office Action.
U.S. Appl. No. 11/293,604, Jun. 17, 2009 Non-Final Office Action.
U.S. Appl. No. 11/293,604, Apr. 8, 2009 Amendment and Request for Continued Examination (RCE).
U.S. Appl. No. 11/293,604, Apr. 7, 2009 Amendment after Final Office Action.
U.S. Appl. No. 11/293,604, Jan. 9, 2009 Final Office Action.
U.S. Appl. No. 11/293,604, Sep. 17, 2008 Response to Non-Final Office Action.
U.S. Appl. No. 11/293,604, Jun. 23, 2008 Non-Final Office Action.
U.S. Appl. No. 11/293,591, Aug. 14, 2007 Notice of Allowance.
U.S. Appl. No. 11/293,605, Jun. 23, 2010 Notice of Allowance.
U.S. Appl. No. 11/293,605, Mar. 22, 2010 Request for Continued Examination (RCE).
U.S. Appl. No. 11/293,605, Dec. 22, 2009 Notice of Allowance.
U.S. Appl. No. 11/293,605, Nov. 23, 2009 Amendment and Request for Continued Examination (RCE).
U.S. Appl. No. 11/293,605, Oct. 28, 2009 Response to Final Office Action.
U.S. Appl. No. 11/293,605, May 22, 2009 Final Office Action.
U.S. Appl. No. 11/293,605, Jan. 26, 2009 Response to Non-Final Office Action.
U.S. Appl. No. 11/293,605, Sep. 24, 2009 Non-Final Office Action.
U.S. Appl. No. 11/293,605, Sep. 3, 2008 Amendment after Final.
U.S. Appl. No. 11/293,605, Aug. 25, 2008 Advisory Action.
U.S. Appl. No. 11/293,605, Aug. 4, 2008 Response to Final Office Action.
U.S. Appl. No. 11/293,605, Mar. 24, 2008 Final Office Action.
U.S. Appl. No. 11/293,605, Dec. 14, 2007 Response to Non-Final Office Action.
U.S. Appl. No. 11/293,605, Sep. 20, 2007 Non-Final Office Action.
U.S. Appl. No. 11/293,603, Dec. 11, 2009 Amendment and Request for Continued Examination (RCE).
U.S. Appl. No. 11/293,603, Jun. 11, 2009 Final Office Action.
U.S. Appl. No. 11/293,603, Apr. 29, 2009 Response to Non-Final Office Action.
U.S. Appl. No. 11/293,603, Dec. 10, 2008 Non-Final Office Action.
U.S. Appl. No. 11/293,592, Sep. 8, 2011 Notice of Allowance.
U.S. Appl. No. 11/293,592, Aug. 23, 2011 Request for Continued Examination (RCE).
U.S. Appl. No. 11/293,592, Aug. 19, 2011 Response to Amendment under Rule 312.
U.S. Appl. No. 11/293,592, Aug. 16, 2011 Amendment after Notice of Allowance.
U.S. Appl. No. 11/293,592, Jul. 7, 2011 Response to Amendment under Rule 312.
U.S. Appl. No. 11/293,592, Jun. 22, 2011 Amendment after Notice of Allowance.
U.S. Appl. No. 11/293,592, Jun. 20, 2011 Notice of Allowance.
U.S. Appl. No. 11/293,592, May 26, 2011 Response to Non-Final Office Action.
U.S. Appl. No. 11/293,592, Nov. 26, 2010 Non-Final Office Action.

(56) References Cited

OTHER PUBLICATIONS

U.S. Appl. No. 11/293,592, Aug. 5, 2010 Amendment and Request for Continued Examination (RCE).
U.S. Appl. No. 11/293,592, Feb. 5, 2010 Final Office Action.
U.S. Appl. No. 11/293,592, Dec. 14, 2009 Response to Non-Final Office Action.
U.S. Appl. No. 11/293,592, Dec. 2, 2009 Notice of Non-Compliant.
U.S. Appl. No. 11/293,592, Aug. 13, 2009 Response to Non-Final Office Action.
U.S. Appl. No. 11/293,592, Jul. 22, 2009 Notice of Non-Complaint.
U.S. Appl. No. 11/293,592, Apr. 16, 2009 Response to Non-Final Office Action.
U.S. Appl. No. 11/293,592, Nov. 20, 2008 Non-Final Office Action.
U.S. Appl. No. 12/147,172, Aug. 30, 2011 Response to Non-Final Office Action.
U.S. Appl. No. 12/147,172, Mar. 30, 2011 Non-Final Office Action.
U.S. Appl. No. 12/185,430, Sep. 19, 2011 Examiner's Interview Summary.
U.S. Appl. No. 12/185,430, Jun. 20, 2011 Non-Final Office Action.
U.S. Appl. No. 12/185,430, Jun. 10, 2011 Amendment and Request for Continued Examination (RCE).
U.S. Appl. No. 12/185,430, Dec. 10, 2010 Final Office Action.
U.S. Appl. No. 12/185,430, Sep. 16, 2010 Response to Non-Final Office Action.
U.S. Appl. No. 12/185,430, Jun. 18, 2010 Non-Final Office Action.
U.S. Appl. No. 12/421,532, Mar. 28, 2011 Notice of Abandonment.
U.S. Appl. No. 12/421,532, Sep. 3, 2010 Non-Final Office Action.
U.S. Appl. No. 12/421,575, Aug. 23, 2011 Response to Non-Final Office Action.
U.S. Appl. No. 12/421,575, May 24, 2011 Non-Final Office Action.
U.S. Appl. No. 12/421,575, Mar. 9, 2011 Response to Non-Final Office Action.
U.S. Appl. No. 12/421,575, Sep. 9, 2010 Non-Final Office Action.
U.S. Appl. No. 12/421,552, Nov. 24, 2010 Notice of Abandonment.
U.S. Appl. No. 12/421,552, Apr. 26, 2010 Non-Final Office Action.
U.S. Appl. No. 12/421,580, Aug. 24, 2011 Examiner's Interview Summary.
U.S. Appl. No. 12/421,580, Aug. 24, 2011 Response to Non-Final Office Action.
U.S. Appl. No. 12/421,580, Mar. 25, 2011 Non-Final Office Action.
"Statement in accordance with the notice from the European Patent Office Dated 1 Oct. 1, 2007 Concerning Business Methods—EPC / Erklaerung Gemaess Der Mitteilung Des Europaeischen Patentamts Vom 1. Oct. 2007 Ueber Geschaeftsmethoden—EPU / Declaration Conformement AU Communique De L'Office Europ"; Journal Officiel De L'Office Europeen Des Brevets.Official Journal of the European Patent Office. Amtsblattt Des Europaeischen Patentamts, OEB, Munchen, DE; Nov. 1, 2007, pp. 592-593, XP007905525.
Copeland et al., "Generalized Variance Functions to Create Stable and Timely Variances Extimates for Prescription Count Estimates", 2006, Proceedings of the Survey Research Methods Section, American Statistical Association, pp. 2872-2877.
Gaughan et al., "Stability of Jackknife Variance Estimates for Prescription Count Estimates Over Time Intervals" 2006, Proceedings of the Survey Research Methods Sections, American Statistical Association, pp. 3031-3034.

Isaki, Cary T., 1990, "Small-Area Estimation of Economics Statistics," Journal of Business and Economic Statistics, vol. D, No. 4: p. 435-441.
PCT International Preliminary Report on Patentability, Sep. 5, 2008, for application No. US2008/068386.
"Statement in accordance with the notice from the European Patent Office Dated Oct. 1 2007 Concerning Business Methods•—EPC/ Erklaerijng Gemaess der Mitteilung des Europaeischen Patentamts Vom. 1 Oktober 2007 Ueber Geschaeftsmethoden—EPU/Declaration Conformement AU Communique de l'Office Europ; Journal Officiel de l'Office Europeen des Brevets, Official Journal of the European Patent Office, Amtsblattt des Europaeischen Patentamts, OEB, EPC/Erklaerijng Gemaess der Mitteilung des Europaeischen Patentamts Vom. 1 Oktober 2007 Ueber Geschaeftsmethoden—EPU/Declaration Conformement AU Communique de L'Office Europ"; Journal Officiel de L'Office Europeen des Brevets, Oficial Journal of The European Patent Office, Amtsblattt des Europaeischen Patentamts, OEB, Munchen, DE; Nov. 1, 2007, pp. 592-593, XP007905525.
Cochran, 1977, "Sampling Techniques," John Wiley, New York.
Copeland et al., "Generalized Variance to Create Stable and Timely Variances Estimates for Prescription Estimates", 2006, Proceedings of the Survey Research Methods Section, American Statistical Association, pp. 2872-2877.
Gaughan et al., "Stability of Jackknife Variance Estimates for Prescription Count Estimates Over Time Intervals", 2006, Proceedings of the Survey Research Methods Sections, American Statistical Association, pp. 3031-3034.
PCT International Preliminary Report on Patentability for Application No. PCT/US2008/068386, Jan. 5, 2010.
International Search Report for PCT/US05/44398, dated Apr. 3, 2007.
International Search Report for PCT/US05/44394, dated Mar. 31, 2008.
International Search Report for PCT/US05/44395, dated Jul. 16, 2007.
International Search Report for PCT/US05/44399, dated Sep. 11, 2007.
International Search Report for PCT/US05/44396, dated Nov. 8, 2007.
International Search Report for PCT/US08/68386, dated Sep. 5, 2008.
Supplementary European Search Report for EP 05853340, dated Jan. 4, 2010.
Supplementary European Search Report for EP 05853339, dated Apr. 13, 2011.
Supplementary European Search Report for EP 05853342, dated Feb. 2, 2010.
Supplementary European Search Report for EP 05853341, dated Jul. 29, 2009.
Supplementary European Search Report for EP 05853338, dated Sep. 23, 2010.
Isaki, "Small-Area Estimation of Economic Statistics," Journal of Business & Economic Statistics, vol. 8, No. 4 (Oct. 1990), pp. 435-441.
International Search Report for PCT/US05/44397, dated Aug. 22, 2008.

* cited by examiner

SYSTEM AND METHOD FOR DETERMINING TRAILING DATA ADJUSTMENT FACTORS

CROSS-REFERENCE TO RELATED APPLICATIONS

This application is a divisional of and claims the benefit of U.S. patent application Ser. No. 11/293,592 filed Dec. 2, 2005, which claims the benefit of U.S. provisional patent application Nos. 60/646,791, 60/646,811, 60/646,812, 60/646,814, 60/646,815, and 60/646,816, all filed on Jan. 25, 2005. Further, this application is related to U.S. patent application Ser. Nos. 11/293,591, 11/293,602, 11/293,603, 11/293,604, 11/293,605, and 12/185,430, which also claim the benefit of the aforementioned United States provisional patent applications. All of the aforementioned United States patent applications and provisional patent applications are hereby incorporated by reference herein in their entireties.

FIELD OF THE INVENTION

The present invention relates generally to systems and methods for predicting market conditions. The invention in particular relates to systems and methods for predicting market demand for pharmaceutical and other healthcare products.

BACKGROUND OF THE INVENTION

Manufacturers and distributors of retail, wholesale and mail-order products monitor product sales and usage in order to maintain proper inventory and to be able to direct marketing efforts. Product sales are monitored by collecting sales data from wholesale distributors, retail outlets and mail-order facilities and recording this sales data at a central point for evaluation. The collected sales data is analyzed to provide market condition or status reports to the manufacturers and distributors.

In the healthcare industry, millions of healthcare products are prescribed and sold worldwide each day. Prescriptions are written by doctors and filled at pharmacies, medical devices are sold at doctors' offices, hospitals, and pharmacies. Individual businesses participating in various aspects of the pharmaceutical and healthcare industries generate data related to the goods sold to conform to governmental regulations, to track inventory, and track the market share of branded and generic products.

Pharmaceutical entities use data gathered from prescription drug outlets to improve their understanding of the ever-changing healthcare product marketplace. In particular, these business entities pay attention to information on the use (e.g., type of drug, dosage, number of doctors writing prescriptions per pharmacy, etc.) of specific products and product categories so that they can produce, supply and stock of such products at outlets (retailers, doctors, etc.) in a timely manner. Monitoring of healthcare markets involves sampling sales at retail outlets and transferring sales data to a central point for evaluation and analysis. Product demand estimates may be based on such analysis. Retail outlets usually cooperate in providing sales data but a significant number of retail outlets are not able to or do not elect to have sales data sampled in a form needed for analysis. As a result, it is necessary to estimate product sales of unsampled and poorly sampled individual outlets to provide marketing information.

Estimates of business sales in small areas, such as counties of a state, have been made based on known data for the state under the assumption that the relationships for the state also hold for the county. The article "Small-Area Estimation of Economic Statistics" by Cary T. Isaki, Journal of Business and Economic Statistics, Vol. D, No. 4, October, 1990, pages 435-441 describes a ratio correlation (multiple regression) approach for estimating retail sales for small areas (counties) using county-to-state shares of retail sales from two successive economic censuses. While these methods provide estimates of retail sales over a relatively small county area from publicly available data, they are not adapted to estimate retail sales of individual outlets.

Estimation of physician prescribing activity has been attempted by marketing researchers based on ratio estimators and inflation factor estimators as commonly described in texts such as "Sampling Techniques" by W. G. Cochran, John Wiley, New York 1977. These methods attempt to estimate the activity in a pre-established geographic area of known dimensions by scaling up a sample of activity within the area in proportion to the level of a known auxiliary variable (i.e., ratio estimate) or in proportion to the level of sample coverage (via an inflation factor) for the entire area. Typical geographic areas encompass a number of outlets and prescribers. Such geographic-based methods do not yield estimates of each individual prescriber's activity within each individual outlet but only produce a measure of the total activity for the geography. If prescriber level estimates are desired, these methods must assume that the proportion of the total activity that is captured in the sample data (i.e., the captured proportion) of each prescriber is the same. If outlet estimates are desired, it must then be assumed that each unsampled outlet is accurately represented by the average of the sampled outlets in the geography. With these assumptions, all sample data within a stratum receive the same "scale-up" factor. These assumptions, however, are known to be false and result in biased estimates at the activity source level.

U.S. Pat. No. 5,781,893 describes systems and methods for estimating sales activity of a product at sales outlets including "sampled" outlets and "unsampled" outlets (i.e., at outlets at which sales activity data is sampled, and not sampled, respectively). Sales activity at unsampled outlets is estimated by determining the distances between each of the sampled outlets and each of the unsampled outlets and correlating sales activity data from the sampled sales outlets according to the determined distances. The sales activity of the product at the sampled outlets and the estimated sales activity of the product at the unsampled outlets are combined to obtain an estimate of sales activity at all the sales outlets. Sales activity of products prescribed by a physician at both the sampled and unsampled outlets can be estimated by correlating sales activity data for a prescribing physician at the sampled outlets. Sales information for specific products at particular outlets is estimated on a monthly or weekly basis with reference to historical use information.

Projection estimates for immediate or near term demand for prescription drugs or products, are based on historical data (e.g., pharmaceutical sales and dispensed product data) that is obtained from product outlets (e.g., dispensing pharmacies). Pharmaceutical companies may use this demand estimate (i.e. a month or week's predicted demand) to guide them to manufacture and supply stocks of the specific products to the dispensing outlets in a timely manner. If a particular outlet did not report data for a particular month, the prior art estimation methods use data previously reported by other reporting outlets to estimate the current month or week's demand. The prior art manner of data reporting in the health care industry is on a national level, but not specific to a particular drug at a particular pharmacy in a particular location.

While the prior art techniques were useful in slowly changing markets, such estimation techniques are no longer reliable or suitable for rapidly shifting market conditions in which pharmaceutical companies now operate. There is outstanding need for rapid and detailed forecasts of the demand of pharmaceutical and healthcare products in the market.

Co-assigned pending U.S. patent application Ser. No. 09/730,266 filed Dec. 5, 2005, which is incorporated by reference herein in its entirety, describes systems and methods for estimating product distribution using a product specific universe.

Further consideration is now being to improving systems and methods for forecasting market demand for products. In particular, attention is directed to improving short term or near term forecasts of product demand. Desirable systems and methods will provide accurate and reliable predictions or forecasts of the demand of a particular drug at a particular pharmacy in a particular location.

SUMMARY OF THE INVENTION

Forecasting systems and methods are provided for accurate and reliable prediction of the demand of a particular drug at a particular pharmacy in a particular location. The systems and methods involve analysis of sample data at product levels or other fine levels of the product market/distribution structure. The analysis includes continuous evaluation and recalibration of sample data and prediction models on which near term demand forecasts are based. The predictions and models which they are based on are updated dynamically in response to incoming market data.

The forecasting systems and methods may be advantageously utilized by pharmaceutical market researchers to understand and respond to the ever-changing healthcare market based on product level data. The product level market data (e.g., prescription (Rx) data) is obtained from prescription drug outlets. Market data (e.g., products sold or dispensed data) is obtained from a number of "sample" or "reporting" outlets that, for example, can make such data readily available. The market data may cover any suitable time (e.g., week or month). Market data or conditions for "non-reporting" outlets are estimated from the reporting outlets' data. The forecasting systems and methods forecast market conditions or data as a function of projected product-level prescription information and sales information for all the sample and non-sample outlets Incoming market data from reporting outlets (e.g., for a current week forecast) is combined with previously calculated projection factors to create new projection factors for the current week. The new projection factors are used to project the product sales for the sample stores. Based on both the reported and projected sales data for the sample stores, the product level distribution factors are computed. These product level distribution factors are used to project the prescription sales for all non-sample outlets.

The set of outlets under consideration may be referred to herein interchangeably as the "universe" or "store universe." A weekly or monthly forecasting process itself may be referred to herein as "sizing of universe stores."

In accordance with one aspect of the present invention, Current week estimate or forecasts and collected sample data reports are generated on a weekly and daily basis. Current week estimates or forecasts are kept in a shadow database. In this manner, the forecasting systems may continually predict the present week's sample data even as the data for the present week is reported.

In accordance with another aspect of the present invention, the actual data for the present week may be compared to the present week's predicted data for each reporting entity. The predicting model may be improved or adjusted based on the difference between the predicted data and the reported data.

In accordance with still another aspect of the present invention, an adjustment factor (i.e., a calibration factor) may be determined. General quality control applications may be used to determine if the reported data appears unusual, e.g., due to a result of an outbreak of a virus, a catastrophe, or a drug recall. The adjustment factor is used to adjust the predicted near term demand for the non-reporting entities, for example, the demand for the present week or the remainder of the present week.

BRIEF DESCRIPTION OF THE DRAWINGS

Further features of the invention, its nature, and various advantages will be more apparent from the following detailed description of the preferred embodiments and the accompanying drawings, wherein like reference characters represent like elements throughout, and in which.

DETAILED DESCRIPTION OF THE INVENTION

Forecasting systems and methods are provided for accurate and reliable near term prediction of the product demand. The systems and methods can be advantageously used to forecast demand of a particular drug at a particular pharmacy in a particular location. The forecasts are based on data collected from reporting or "sample" stores or market outlets. The systems and methods involve continuous evaluation and recalibration of sample data collected from market outlets. The prediction models on which near term demand forecasts are based also may be dynamically updated or adjusted in time.

Figure 1A:
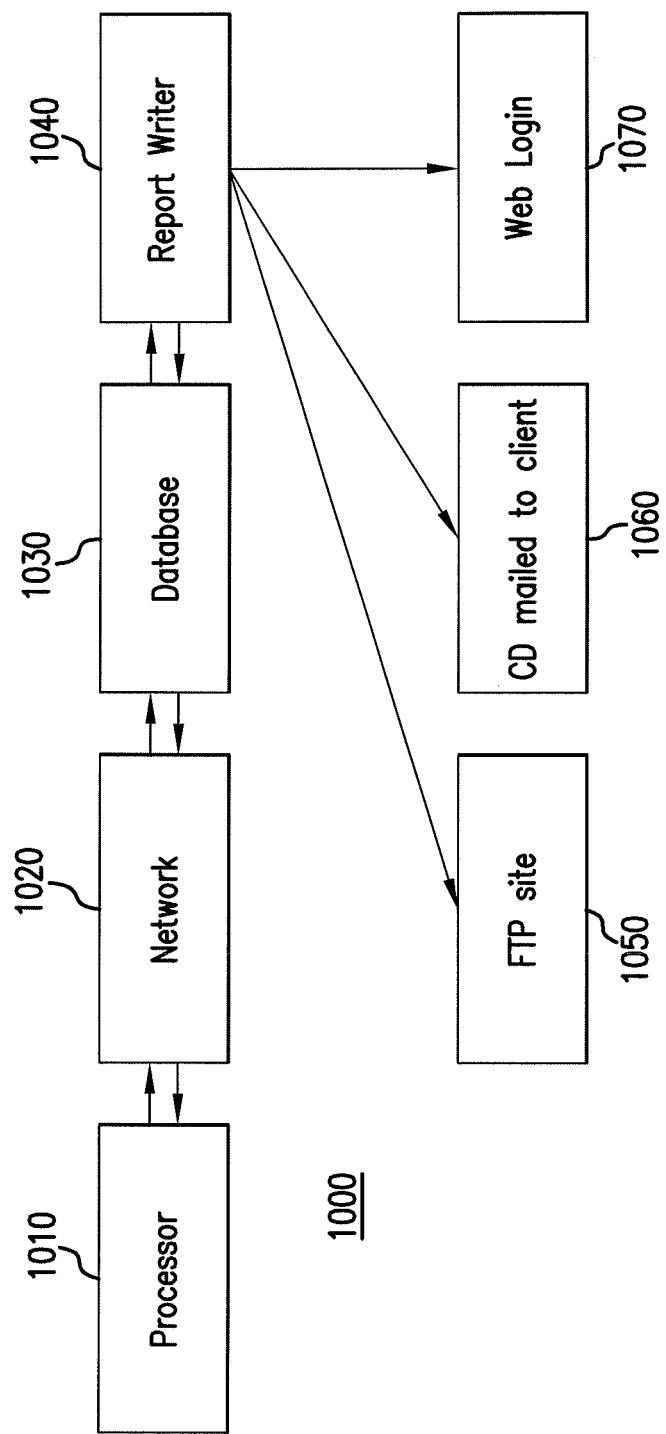
FIG. 1A is a block diagram of the components of a system for predicting market demand in accordance with the principles of the present invention.

FIG. 1A shows an exemplary forecasting system 1000 for predicting market demand. Forecasting system 1000 includes a processor 1010, a database 1030 (e.g., Oracle database) and a report generator or writer 1040. Processor 1010 may communicate with database 1030 and report generator 1040 via suitable electronic links, for example, a network 1020. System 1000 generates forecasts or predictions of market conditions (e.g., product demand or other information), which are then provided to clients (e.g., product manufacturers). The market information may be formatted or assembled by report writer 1040 into a report for delivery to the clients. The report may be provided as a hardcopy and/or in a dataset format. System 1000 may include suitable access interfaces (e.g., FTP 1050, CD 1060, or Web login 1070), which may be utilized by the clients for viewing the reports.

Figure 1B:
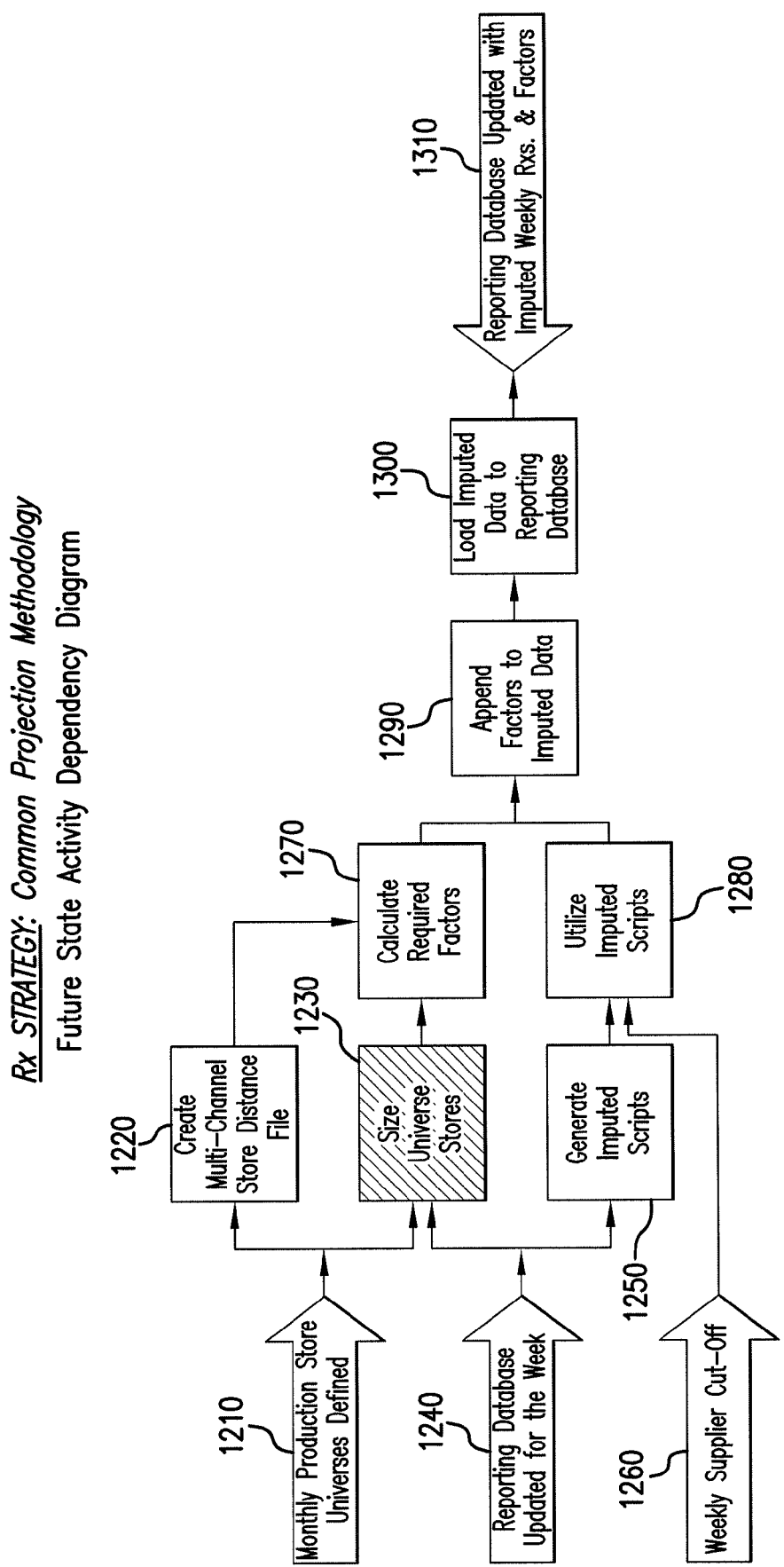
FIG. 1B is a block diagram of elementary business processes that are interlinked in a common market projection methodology in accordance with the principles of the present invention.

FIG. 1B shows a block diagram of interlinked elementary business processes ("EBP") 1210-1310 in a market projection methodology that is supported by the inventive forecasting systems and methods. Interlinked EBPs 1210-1310 may be conducted contemporaneously in parallel or in series as appropriate for monitoring and cyclically (e.g., weekly) predicting market conditions. With reference to FIG. 1B, process 1210 involves, for example, a definition of monthly production store universes. Following process 1210, process 1220 involves creating or generating multi-channel store distance files, and process 1230 involves sizing the universe stores. Processes 1220 and 1230 lead to process 1270 for calculating required projection factors. Process 1240 involves updating the Reporting database for a subject week and leads to process 1230 and process 1250. The latter process 1250 involves generating imputed scripts and in combination with process 1260 ("weekly supplier cutoff") leads to process 1280 for utilization of the imputed scripts. Required projection factors calculated at process 1270 are appended to the imputed data in process 1290. This data is then loaded to the reporting database (process 1300). In process 1310, the reporting database is updated with imputed weekly prescriptions (Rx) and factors.

Figure 2:
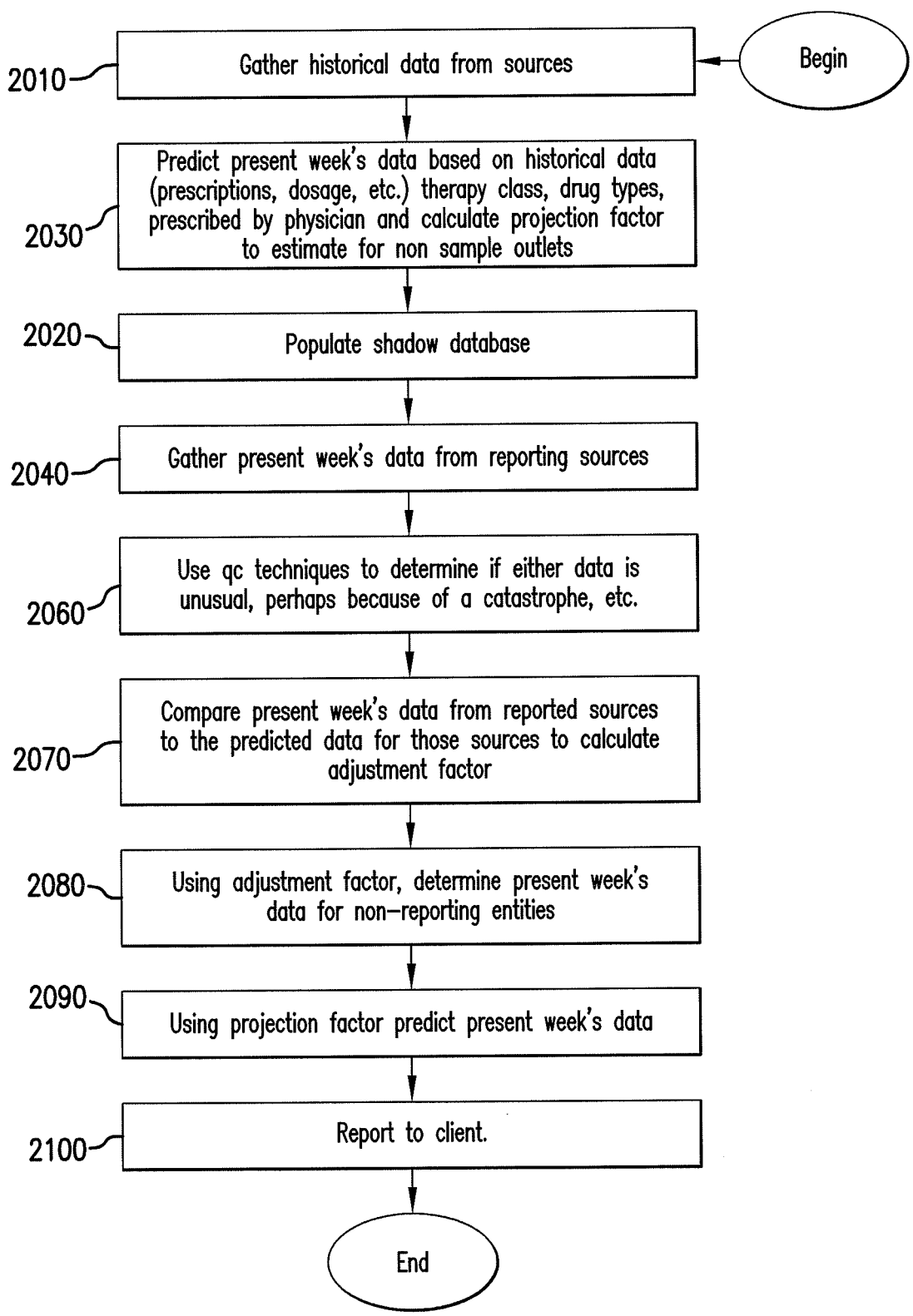
FIG. 2 is a flow diagram illustrating the steps of an exemplary process for predicting market demand in accordance with the principles of the present invention.

FIG. 2 shows an exemplary "store sizing" process 2000 for predicting market conditions or product demand using system 1000 of FIG. 1A. Process 2000 utilizes historical market data gathered from any number of "sampling" sources, including for example, retail and software vendors to provide initial or preliminary forecasts. The historical data may be assembled in database 1030. At step 2010, process 2000 reads or collects the historical data from the database 1030. The collected historical data is reassembled in, for example, an extended database segment in the database 1030. At step 2030, process 2000 uses a suitable financial or business model to predict or generate a preliminary forecast of the product demand based on the historical data from sampling sources (i.e. sample pharmacy stores or outlets). The forecast may cover any suitable time interval (e.g., the current or present week). At step 2030, process 2000 also calculates a projection factor to estimate product sales or demand for non-sample outlets. The present week's predicted product sales or demand ("Weekly Forecast") may include forecasted values for a select set of parameters (e.g., the number of prescriptions of a particular product, the dosage, and the number of prescriptions written by a certain doctor. At step 2020, the Weekly Forecast (including the forecasted values for the selected set of parameters) is stored in a shadow database. The shadow database may have any convenient structure or format (e.g., a relational database or table, or flat files).

The Weekly Forecast is a work-in-progress and is continually updated by process 2000. At step 2040, "live" market data is gathered from a group of reporting sources (i.e., sample outlets) during a time interval. This time interval may include or overlap with all or some of the time (e.g., days of the week) that is the subject of the Weekly Forecast. At step 2060, the live data may be subject to quality control routines or algorithms to screen or note any of the live data, which may be due to an unusual event, for example, a result of a catastrophe, flu outbreak, etc. Then at step 2070, process 2000 compares the live data with forecasted data in the Weekly Forecast for the group of reporting outlets, and accordingly calculates an adjustment factor. The adjustment factor is based on the difference between the live data and the predicted data in the Weekly Forecast for the group of reporting sources.

The adjustment factor may be calculated on a product-level, a local geography level, a product dosage level, or Prescriber level, or any other suitable or appropriate market definition category or subcategory. A product level may, for example, refer to specific products, which are identified by a corresponding "CMF" descriptor (e.g., Lipitor). Process 2000 then updates the Weekly Forecast stored in the shadow database using the calculated adjustment factor. For example, at step 2080, process 2000 may update data entries for non-reporting outlets stored in the shadow database using the adjustment factor obtained at step 2070 and other relevant data. Process 2000 then readjusts (e.g., iteratively recalculates) the Weekly Forecast stored in the shadow database (step 2090). At step 2100, the updated the Weekly Forecast is provided to clients so that they can rapidly respond to changing market conditions.

Figure 3A:
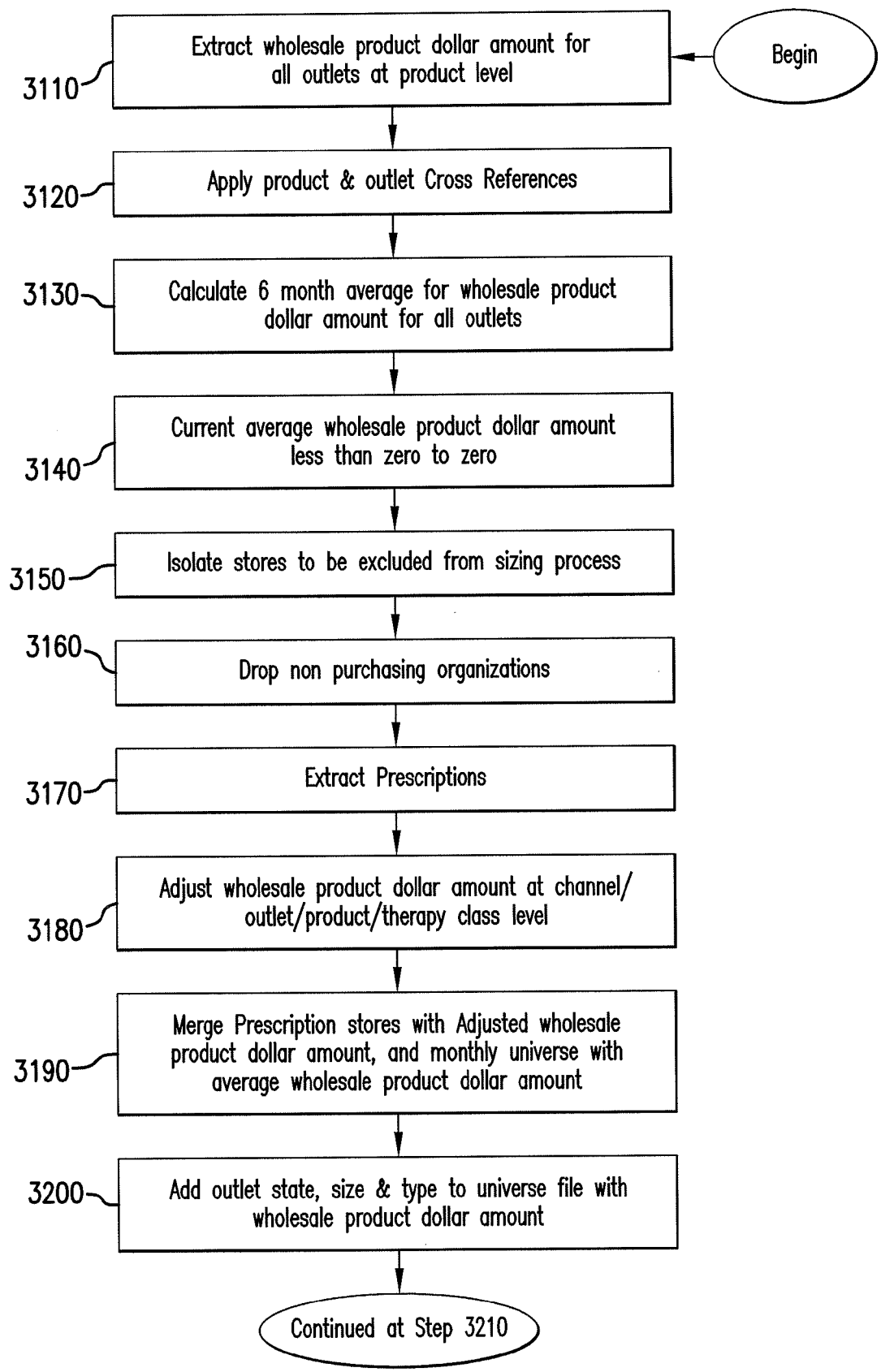
FIG. 3 is a flow diagram illustrating details of an exemplary process for predicting market demand in accordance with the principles of the present invention.
Figure 3B:
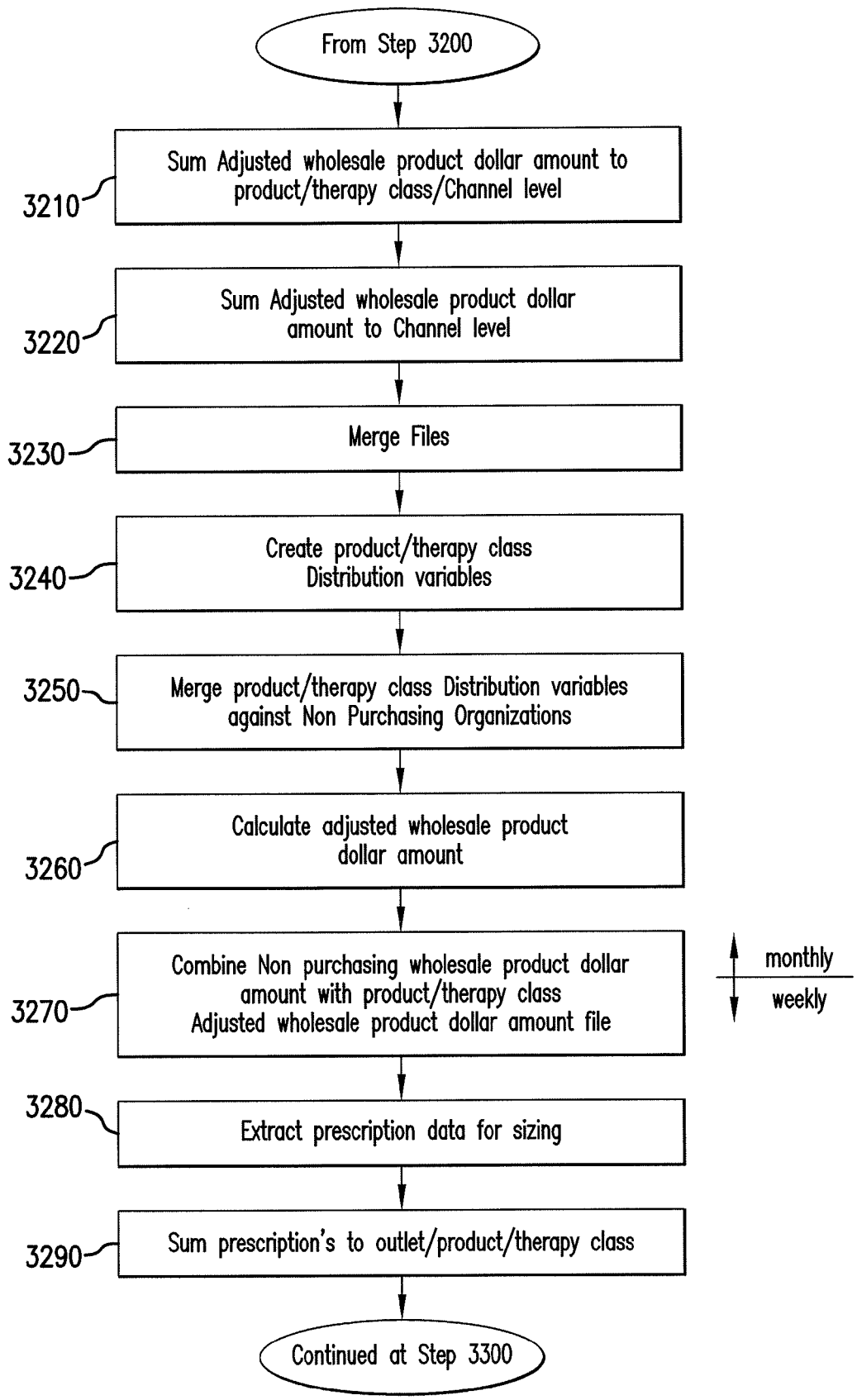
Figure 3C:
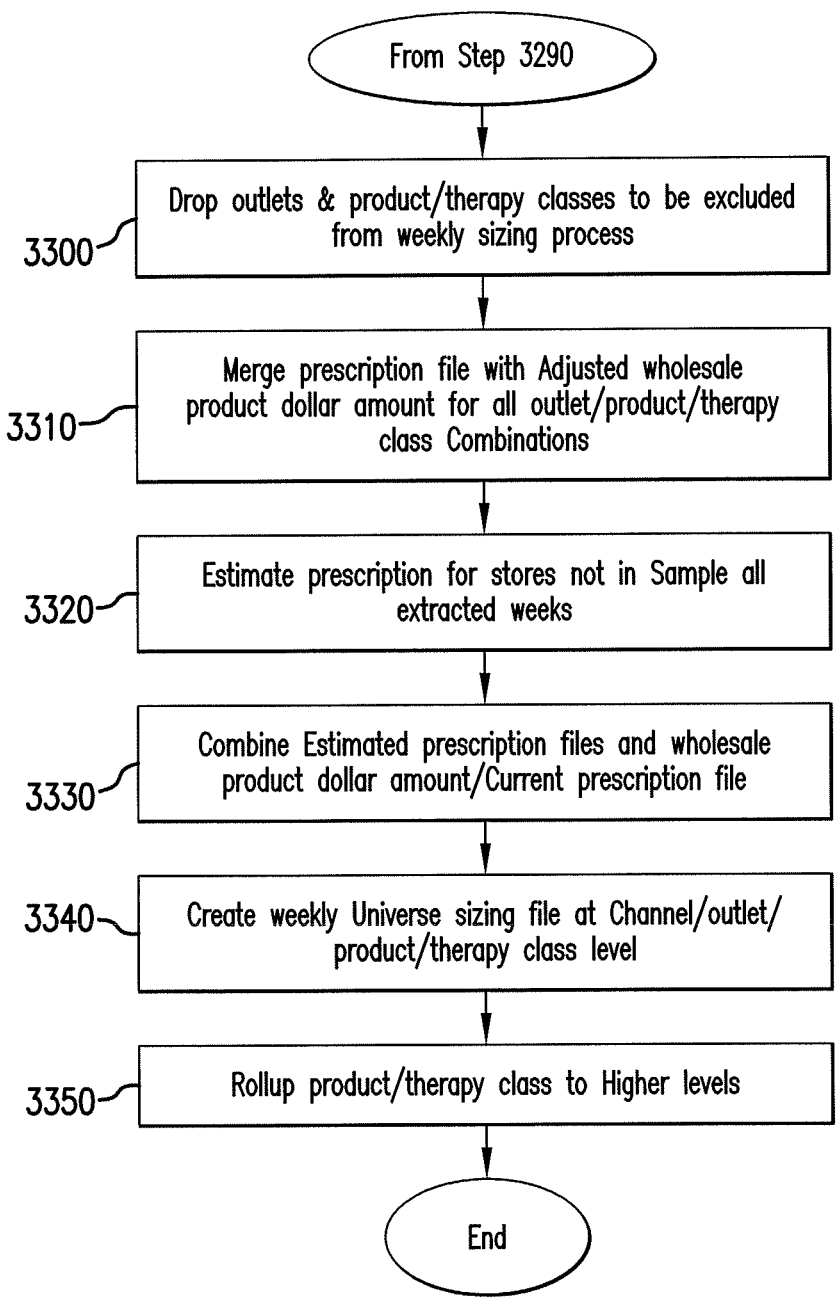

FIG. 3 show details of an exemplary store sizing procedure 3000 that may be used in process 2000. Utilizing a DDD History File, the system may extract DDD $ data at the outlet/CMF 10 level for all outlets in the universe. For example, at step 3110 in procedure 3000, process 2000 may extract wholesale product dollar sales amounts ("DDD$" or "wholesale amounts") from a wholesale product sales history file. The wholesale amounts may be categorized by outlet and/or drug product levels for all product channels and outlets in the subject store universe (e.g., the entire population of outlets including Retail, Long Term Care and Mail Order Universes, etc.). It will be understood that the wholesale amounts may be negative, for example, in the case of product returns or refunds.

At step 3120, product and outlet cross-reference data may be utilized to reflect changes to outlet and/or product information. Accordingly, the wholesale amounts may be consolidated under current outlet and product numbers, for example, by combining or eliminating outlets and product not in the current or subject market universe. At step 3120, for example, DDD $ amounts may be consolidated under current CMF outlet and CMF product numbers, split outlet DDD$ may be combined, and outlets in the current Retail, Long Term Care and Mail Order Universes may be eliminated.

At step 3130, running six-month average wholesale amounts are computed using the consolidated wholesale amounts. The running six-month averages may be computed monthly for a number of months (e.g., for six months) preceding the latest month for which sales data is available.

After calculating the six-month average wholesale amounts for all outlets, procedure 3000 at step 3140 may reset any negative average wholesale amounts to zero. Procedure 3000 may be configured to generate a "Wholesale dollar Amounts" data file (e.g., a "DDD$" file) listing wholesale amounts by product/therapy class level for each outlet or channel. For each outlet or channel, a product/therapy class level data record may include, for example, channel identifier; a retail outlet identifier; a product identifier (e.g., a CMF7 descriptor); a therapy class identifier (e.g., a USC 1-5 descriptor); and average wholesale product dollar sales information. A therapy class is understood to mean a type or category of drugs directed to a therapy or treatment, i.e., cholesterol reducers, high blood pressure treatment, etc.

Certain stores may be excluded from store sizing procedure 3000 based, for example, on experience or traditional considerations. At step 3150, data related to such stores are identified and isolated in the Wholesale Amounts file before further processing. The data related to these excluded stores may be segregated and written to a separate data file (e.g., Excluded Stores File). The Excluded Stores File data may be remerged with the Wholesale Amounts file at the end of the procedure 3000 (e.g. monthly). The Excluded Stores File may also include data related to stores that have atypical or abnormal wholesale product sales information. A projection factor of "1" may be assigned to each sample store excluded from the sizing process (procedure 3000).

Further, at step 3160, the Wholesale Amounts file may be vetted to remove or isolate information related to all non-purchasing organizations. For convenience in data processing, a list of non-profit purchasing organizations may be stored in a file or table. The list of non-purchasing organizations may be created by using a non-wholesale product sales/ non-prescription warehouse sizing process.

Next at step 3170 in procedure 3000, all good and imputed total prescription data is extracted from a total prescriptions data file. The total prescriptions data for non-purchasing organizations and "excluded" stores may be removed from further processing in a manner similar to data excluded from the Wholesale Amounts file at steps 3150 and 3160.

Procedure 3000 then applies adjustments the wholesale amounts at the channel, outlet, product, and/or therapy class levels (step 3180). Procedure 3000 may be configured to perform the adjustments at one or more of these levels. The adjustments may include retaining total prescription data (TRx) for stores that were in the sample every week in the extracted time period, running a cross-reference to pick up the latest drug product codes (e.g., CMF-10) and proprietary therapy classes (USC5), summing the total prescription counts to the channel/outlet/product (CMF7)/therapy class (USC5) level for this time period; and merging on the average wholesale product dollar amount for these records only.

Procedure 3000 may generate a combined total prescription and adjusted wholesale amounts file at step 3190. The combined or adjusted prescription/wholesale amounts file (e.g., "TRx/DDD $" file) may be include total prescriptions (TRx) and wholesale amounts (DDD$) information categorized by channel, outlet, and product/therapy class. The data in the files may be formatted or extended to include, for example, a one-byte outlier field to an adjusted wholesale product dollar amount file.

Procedure 3000 may generate an adjusted wholesale amounts file with adjusted wholesale product dollar amounts for each outlet with total prescriptions greater than zero. The output file may be formatted to contain the following fields: channel; outlet; product/therapy class (CMF7/USC5); total prescriptions (TRx); wholesale product dollar amount (e.g. DDD$); and estimated wholesale product dollar amount (e.g. Estimated DDD$).

Procedure 3000 determines if an outlet's estimated wholesale product dollar amount (Estimated DDD$) should replace its actual wholesale product dollar amount, and accordingly generates the adjusted wholesale product dollar amount file ("Adjusted DDD$ file"). This file may contain the following fields: channel; outlet; product/therapy class (CMF7/USC5); wholesale product dollar amount (DDD$); adjusted wholesale product dollar amount (Adjusted DDD$); and an outlier identifier.

To adjust the wholesale product dollar amounts for all outlets having total prescriptions greater than zero, procedure 3000 cycles through data records having a product dollar amount greater than zero, for each of the outlet, product and therapy classes. A "Regression Factor" is computed at the channel/product/therapy class levels by regression analysis of the total prescriptions and the wholesale product dollar amounts. An exemplary function that may be used for regression analysis is:

$$\text{Regression\_Factor} = (\text{sum of total prescriptions} * DDD) / \text{sum}(DDD * DDD) \quad (1)$$

The computed or fitted Regression_Factor may be merged back into the "TRx/DDD" file by channel/product/therapy class for all outlets. Procedure 300 may generate an Estimated Wholesale Product Dollar Amounts file based on the Regression_Factors. Entries in the Estimated Wholesale Product Dollar Amounts may be calculated by multiplying the Regression_Factors with the total prescriptions. Procedure 300 may also calculate the standard deviation of the estimated wholesale product dollar amount. Any suitable statistical programs or routines may be used for regression analysis. A suitable statistical program, which is a commercially available, is a statistics calculations program SAS 8.2.

Procedure 3000 then evaluates if the estimated wholesale product dollar amount should replace the actual wholesale product dollar amount based on statistical criteria and rules. For example, if the estimated wholesale product dollar amount is within three standard deviations of the actual wholesale product dollar amount, then the adjusted wholesale product dollar amount may be set equal to the actual wholesale product dollar amount. Conversely, if the estimated wholesale product dollar amount is not within three standard deviations of the actual wholesale product dollar amount, the adjusted wholesale product dollar amount may be set equal to the estimated wholesale product dollar amount. The outlier field in the data record may be set positive (e.g., "yes") to indicate such replacement. If after such replacement or otherwise, the adjusted wholesale product dollar amount is less than a preset minimum wholesale product dollar amount, procedure 3000 may delete the data record.

Procedure 3000 may merge the total prescription/stores adjusted DDD$ file with the monthly universe with average wholesale amounts file (step 3190). The merger may be indexed based upon a key for each record of each input data file. Procedure 3000 may keep the wholesale product dollar amount and outlier flag record in the merged file when a key is in both input files. In the event the key is not on both input files, procedure 3000 may indicate as much by resetting the outlier field byte (e.g., to "blank" "space"), and adjust the wholesale product dollar amount to equal the wholesale product dollar amount. In merging the noted input files, procedure 3000 may create a Final Monthly Universe file with Average wholesale product dollar amount file.

At step 3200, procedure 3000 may add the outlet's state, size and type data to the Universe file having wholesale product dollar amounts information to generate a Total universe file with adjusted wholesale product dollar amounts (step

3200). In the event, a channel does not include the outlet's type or size, this variable may be ignored in further processing.

At step 3210, procedure 3000 may sum the adjusted wholesale product dollar amount at the following levels: Channel/Size/Type/State/Product (CMF7)/Therapy Class(USC5); Channel/Size/Type/Product/Therapy Class; Channel/Size/Product/Therapy Class; and Channel/Product/Therapy Class. The sequence/hierarchy of the size, type and state fields may be based on monthly parameters. These "parameters" may be provided by or obtained form channel data fields. For the summing procedure, it will be understood, that a parameter is a constant that can be changed in program code. By "sum . . . at the following levels," it will be understood that a process of adding numeric values at all possible combinations of levels is performed indexed at one of the listed levels.

At step 3210, procedure 3000 may then sum the adjusted wholesale product dollar amount to channel level, e.g., at the following levels: Channel/Size/Type/State/; Channel/Size/Type; and Channel/Size (step 3220). Again, the sequence/hierarchy of the size, type and state fields may be based on monthly parameters. These parameters may be provided in channel data.

At step 3230, procedure 3000 may merge the Total Universe file having adjusted wholesale product dollar amount summed to channel with the Total Universe File having adjusted wholesale product dollar amount summed to product/therapy class/channel. Procedure 3000 may generate a named product name (i.e., a named CMF7 drug) file (i.e., the final monthly universe with adjusted wholesale product dollar amount file). The named drug file may include the following fields: channel/product (CMF7)/therapy class (USC5); size (may be blank); type (may be blank); state (may be blank); product/therapy class adjusted wholesale product dollar amount (CMF7/USC5 Adjusted DDD$); total adjusted wholesale product dollar amount; and total outlet count.

Utilizing the named CMF7 file, procedure 3000 may generate product/therapy class_distribution variable for each product/therapy class (CMF7/USC5) using empirical rules at step 3240. According to an exemplary rule, a product/therapy class_distribution variable may be created as follows for each channel/product/therapy class: if the outlet count is greater than a channel distribution outlet count, then:

product/therapy class_distribution=(Drug/therapy class Total Adjusted wholesale product dollar amount file/Adjusted wholesale product dollar amount file), however, if the Outlet count is less than or equal to the channel distribution outlet count, then:
the record is deleted.

Procedure 3000 may generate a drug/therapy class distribution file that includes the following fields: channel/product/therapy class; size (may be blank for higher levels); type (may be blank for higher levels); state (may be blank for higher levels); and product/therapy class_distribution.

Further at step 3250, procedure 3000 may merge the product/therapy class_distribution value with a non-purchasing organization file having store wholesale product dollar amount, using the following hierarchy (if the select level is not available): State/size/type; size/type; size; all. The merge product/therapy class distribution values against non-purchasing organizations process may require the non-purchasing organization file with store wholesale product dollar amount. This file may be created by using the non-wholesale product sales/non-prescription warehouse sizing process.

Next at step 3260, procedure 3000 may calculate Adjusted wholesale product dollar amounts as follows:

Adjusted wholesale product dollar amount (Adjusted DDD $)=product/therapy class_Distribution*Outlet wholesale product dollar amount.

At step 3260, procedure 3000 may generate a non-purchasing wholesale product dollar amount file that will include the following fields: channel, outlet, product/therapy class, wholesale product dollar amount, and adjusted wholesale product dollar amount.

At step 3270, procedure 3000 may combine the non-purchasing wholesale product dollar amount file generated at step 3260 with the final monthly universe having adjusted wholesale product dollar amount file generated at step 3230, and the "stores excluded from monthly sizing generated at step 3150. Procedure 300 also may set the outlier equal to "blank" and adjusted wholesale product dollar amount equal to wholesale product dollar amount, and further run product cross-references to pick up the latest drug products and therapy classes. The combined file may contain wholesale product sales data for all outlet/product/therapy class combinations in the universe. Step 3270 completes the monthly store sizing process portion of procedure 3000.

With continued reference to FIG. 3, step 3280 represents the start of the weekly sizing process portion of procedure 3000. From the updated reporting database, procedure 3000 may extract raw (both actually reported and imputed) total prescription data for all outlets from the predefined number ("W") of weeks of data. Only data from stores that had good or imputed prescription data in all extracted weeks may be kept or processed. Step 3280 may also involve running product cross-references to pick up the latest drug products (CMF10) and therapy classes (USC5).

Using the total prescription data extracted at step 3280, procedure 3000 may next at step 3290 sum the total prescriptions to the outlet/product/therapy class level and then divide the sum of the total prescriptions by the number of weeks parameter value W to obtain average total prescriptions ("Average TRx"). The field size of the average total prescriptions field in the data records may, for example, be eight (8) whole and four (4) decimal places.

At step 3300, procedure 3000 may remove stores and products that have been designated for exclusion from the weekly sizing process using the total prescriptions summed to outlet/product/therapy class file. For this purpose, procedure 3000 may further utilize "the stores excluded from monthly sizing process" and "products (CMF7s) requiring therapy class (USC5) level projections" files.

Next at step 3290, procedure 3000 may merge the weekly total prescription data summed to the outlet/drug (CMF7)/therapy class (USC5) level file with the monthly-adjusted wholesale product dollar amount for all outlet/product/therapy class combinations in universe file generate at step 3270 using the following rules:

1) if the outlet/product/therapy class is present on the wholesale product dollar amount monthly file and not on the total prescriptions weekly file, then the system may ignore the outlet; and 2) if the outlet/product/therapy class is present on the total prescriptions weekly file and not on the wholesale product dollar amount monthly file, then the system may set wholesale product dollar amount equal to zero Procedure 3000 may use the monthly file that matches the first day of the week when conducting the weekly sizing process, and every week of a given month will use the same monthly file. For example, if the first day of the week is November 27, the November monthly file may be used in the weekly sizing process for that week as well as all other weeks whose first day has a November date. Similarly, if the first day of the week is December 1, the December monthly file may be used in the weekly sizing process for that week as well as all other weeks whose first day has a December date. Procedure 3000 may at step 3280 generate a wholesale product dollar amount/total prescriptions file that will include the following fields: channel, outlet, product/therapy class (CMF7/USC5), wholesale product dollar amount, adjusted wholesale product dollar amount, and total prescriptions. At step 3290, procedure 3000 may sum all product/therapy classes with total prescriptions greater than zero to identify the potentially missing population and identify all outlets with no total prescriptions.

Based on the wholesale product dollar amount/total prescriptions file created at step 3290, procedure 3000 may at step 3320 estimate total prescriptions for stores not in the sample all extracted weeks. First at step 3300, procedure 300 drops all outlets and product/therapy classes that are to be excluded from weekly sizing processes. Step 3320 results in an output file of sample stores only with adjusted wholesale product dollar amounts greater than zero ("Adjusted DDD$>0"). This output file may contain the following fields: channel; product/therapy class; size (may be blank); type (may be blank); State (may be blank); and ratio. Step 3320 may further result in an output file of the estimated total prescriptions for non-sample stores only with the adjusted wholesale product dollar amount greater than zero. This output file may contain the following fields: channel; outlet; product/therapy class; and estimated total prescriptions. Step 3320 may also result in other output files.

An exemplary output file for outlets in the sample all extracted weeks and Adjusted wholesale product dollar amount equal to zero, may contain the following fields: channel/product/therapy class; size (may be blank for higher levels); type (may be blank for higher levels); State (may be blank for higher levels); total prescriptions; and N, where N equals the outlet count represented by total prescriptions.

Another exemplary output file for outlets in the sample all extracted weeks and adjusted wholesale product dollar amount equal to zero may contain the following fields: channel; therapy class; product; size (may be blank); type (may be blank); State (may be blank); and estimated total prescriptions. Yet another exemplary output file of estimated total prescriptions for non-sample stores with adjusted wholesale product dollar amount equal to zero, may contain the following fields: channel; outlet; product/therapy class; and estimated total prescriptions.

With continued reference to step 3320, for all outlets in sample for all extracted weeks with adjusted wholesale product dollar amount greater than zero and outlier not set equal to "Yes," procedure 3000 may sum adjusted wholesale product dollar amount and total prescriptions and get a count of outlets at the following levels: channel; size/type/state/product/therapy class; size/type/product/therapy class; size/product/therapy class; sequence/hierarchy of the size, type and State fields should be based on weekly parameters. These parameters are distinct from the monthly parameters but like the monthly parameters may also be provided by channel.

For processing data records, the parameters N1 and N2 are defined as follows:

$N1$=channel/total prescription/Ratio Outlet Count; and $N2$=channel/total prescription/wholesale product sales ratio cell minimum.

In cases where N1 is less than N2, procedure 3000 may delete the data record. Conversely, for cases where N1 is not less than N2, procedure 3000 may compute a ratio equal to the: (sum of total prescriptions)/(sum of adjusted wholesale product dollar amounts) by channel.

Procedure 3000 may extract the remaining outlet data (all outlets that were not in the sample all of the previous W weeks). Procedure 3000 may merge by the ratio from adjusted wholesale product dollar amount greater than zero file by the lowest hierarchy defined by the parameters. If there is no ratio available, then procedure 3000 may merge by the first parameter noted in parameter file/product/therapy class. Procedure 3000 may continue to the next parameter in noted parameter file/product/therapy class, and then to the product/therapy class level. If there is no data to merge at product/therapy class level, then procedure 3000 may set the ratio equal to zero. Procedure 3000 may calculate estimated total prescriptions using the following equation:

$$\text{estimated total prescriptions} = \text{ratio} * \text{wholesale product dollar amount} \quad (2)$$

Procedure 3000 may produce files for two sets of outlet counts: one count for each channel/state/size/type ("outlet count") and another count for outlets with wholesale product dollar amount greater than zero by product/channel/state/size/type ("product outlet count"). The first file may be merged by channel/state/size/type, and the second file may be merged by product/channel/state/size/type. For any data record for which N is less than N3, where N="DDD$=0 Cell Count"="Outlet Count"−"Product Outlet Count" and N3=DDD$=0 Cell Minimum, then procedure 3000 may delete the data record. The values of N and N3 may be calculated or obtained based on research.

At step 3320, procedure 3000 may calculate estimated total prescriptions (Estimated TRx at each level) using the following equation:

$$\text{estimated total prescriptions} = (\text{sum of total prescriptions})/(\text{total outlet count} - \text{outlet count with wholesale product dollar amount} > 0), \quad (3)$$

where total outlet count=total number of unique outlets in file at that level, and Outlet count with wholesale product dollar amount>0=Unique Outlet Counts by drug (CMF7) from the wholesale product dollar amount>0 file.

If estimated total prescriptions are less than the parameter (total prescriptions size minimum), then procedure 3000 may delete the record.

Next procedure 3000 may extract all outlets that were not in the sample of the previous extracted weeks and wholesale product dollar amount equal to zero from the wholesale product sales/current total prescriptions file.

At step 3320, procedure 3000 may merge on "the estimated total prescriptions from wholesale product sales equal to zero" file by the lowest hierarchy defined by the parameters. If there is no ratio or estimate of total prescriptions available, then procedure 3000 may merge on estimated total prescriptions by channel/size/type/product/therapy class. Procedure 3000 may continue to the channel/size/product/therapy class level. If there is no data to merge at product/therapy class level i.e. CMF7/USC5 level, then procedure 3000 may delete outlet/product/therapy class.

At step 3330, procedure 3000 may combine the estimated total prescriptions file for non-sample stores with wholesale product dollar amount greater than zero, the estimated total prescriptions file for non-sample stores with wholesale product dollar amount equal to zero, and "the wholesale product dollar amount file/current total prescription" file to produce the "weekly universe size" file for the current week. Procedure 3000 may accordingly generate a "weekly universe size" file for the current week that may include the following fields: channel, outlet, product/therapy class, estimated total prescriptions (only for stores not in sample for previous W weeks), and total prescriptions (only for stores in sample for previous W weeks).

Using the universe size files from the current week and previous week, procedure 3000 at step 3340 generates a weekly universe-sizing file at the channel/outlet/product/therapy class level using the following rules:

1) If (current Size/previous Size)>X5 and (current size−previous size)>X7, then current size=previous size*P1; and 2) If (current size/previous size)<X6 and (previous size−current size)>X8, then current size=previous size*P2, where X5=week size change max. ratio, X6=week size change min. ratio, X7=week size change max., X8=week size change minimum, P1=week size change maximum percent, P2=week size change minimum percent, and size=total prescriptions, if a total prescriptions value is available, or size=estimated total prescriptions, if a total prescriptions value is not available.

Procedure 3000 at step 3350 may roll up product/therapy classes to higher levels e.g., to summarize product/therapy class to outlet, product (CMF7), therapy class 5 (USC5), therapy class 4 (USC4), therapy class 3 (USC3), therapy class 2 (USC2), therapy class 1 (USC1), and store, etc. Procedure 3000 may merge the appropriate monthly CPM (retail/long term care/mail order combined) store universe and pick up the store type and monthly sample flag, and create the "weekly universe sizing file for projections" containing the following fields: channel, outlet, store type, monthly sample flag, product sizing level, size.

Figure 4:
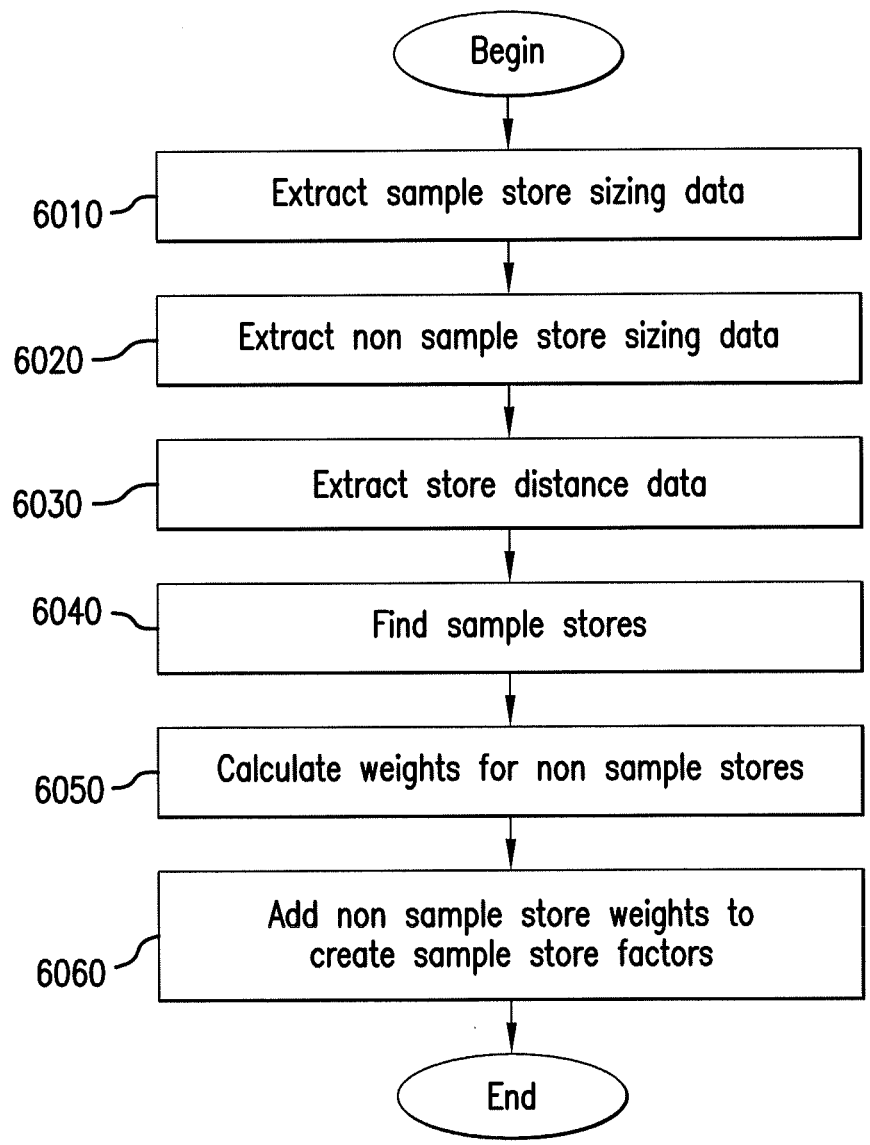
FIG. 4 is a flow diagram illustrating the steps of an exemplary process for calculating a projection factor for predicting market demand in accordance with the principles of the present invention.

FIG. 4 shows an exemplary procedure 6000 for calculating factors for predicting market conditions and data using system 1000 of FIG. 1A. Procedure 6000 is designed to generate projection factors for extrapolating market data from sample stores and outlets to non-sample stores and outlets. System 1000 may be configured, at step 6010 in procedure 6000, to extract all sample stores from a main database file except stores having the following descriptors: a) data imputation override, and/or b) excluded stores from projections parameter.

Outlets associated with a data imputation override descriptor are listed in a data imputation override descriptor file. The sample stores in a repository for input transactions file ("SUSF" file) may have a monthly sample use flag set equal to one. The data imputation override file may contain a list of product outlet identifiers for sample stores that are treated as non-sample stores. The excluded stores from projections parameter file may contain a list of product outlet identifiers for sample stores that are forced to have a projection factor of "1" and are not used to project onto non-sample stores. This parameter may be stored within a production parameter library. A static weekly copy of the production parameter library may be archived (e.g., saved for two years). System 1000 may save the following data for all sample stores that are extracted: product outlet identifier, channel, store type (if retail channel), all product levels identified in the SUSF file for the product outlet identifier, and average total prescriptions for every product level identified in the SUSF file for the product outlet identifier. Drugs or products for which projections will not be created are set to therapy class defaults. Table A shows an example of the saved data

TABLE A

Sample Store Sizing Data

| Sample CMF Outlet # | Channel | Store Type | Product Level | Average TRx |
|---|---|---|---|---|
| 12345678 | R | I | Store | 1000 |
|  |  |  | USC1 | 120 |
|  |  |  | USC2 | 110 |
|  |  |  | USC3 | 200 |
|  |  |  | USC4 | 50 |
|  |  |  | USC5 | 40 |
|  |  |  | CMF7 | 10 |

At step 6020, system 1000 may extract all non-sample stores data from the SUSF file and sample stores in the data imputation override file. The non-sample stores in the SUSF file may have a monthly sample use flag set equal to zero. The data imputation override file may contain a list of product outlet identifiers for sample stores that are treated as non-sample stores. System 1000 may save the following data for all non-sample stores that are extracted: product outlet identifier, channel, store type (if retail channel), all product levels identified in the SUSF file for the product outlet identifier and total prescriptions for every product level identified in the SUSF file for the product outlet identifier. Table B shows an example of the saved data

TABLE B

Non-Sample Store Sizing Data

| Non-Sample CMF # | Channel | Store Type | Product Level | Average TRx |
|---|---|---|---|---|
| 87654321 | R | F | Store | 2000 |
|  |  |  | USC1 | 320 |
|  |  |  | USC2 | 100 |
|  |  |  | USC3 | 90 |
|  |  |  | USC4 | 80 |
|  |  |  | USC5 | 70 |
|  |  |  | CMF7 | 10 |

Next at step 6030, system 11000 may extract the "to" product outlet (i.e. non-sample outlets), the "from" product outlet (i.e. sample outlets) and the distance (miles apart) from a multi-channel store distance file. Based on the extracted data, system 1000 may create a projections store distance file.

Next at step 6040, system 1000 may use "a store distance evaluation process" to find the closest "usable" sample stores in the store distance file for each store (i.e. non-sample stores) for which market conditions need to be projected. The number of sample stores may be restricted to be between a maximum number sample stores parameter and a minimum number sample stores parameter. The sample stores may also be required to be within a distance indicated by a "maximum distance between stores" parameter. A "miles apart" data field value in the store distance data file may determine the closest stores. If the minimum number of sample stores are not found within the distance indicated by the "maximum distance between stores" parameter, then stores that are over that maximum distance may be selected until the minimum number of stores are found in the projection store distance file for the store that needs to be projected. Possibly the minimum number of sample stores may not be found if the number of sample stores that can be selected is limited. Stores that are "usable" or eligible for this purpose may generally refer to stores that are not in "the exclude from projections" list or table, and are not listed in the data imputation override file. The usable stores also must be in an eligible channel for the subject non-sample store. The usable stores eligibility filtering may be done in the store distance process.

All usable stores may be saved and used in a projection formula for calculate weights. The maximum number sample stores parameter may contain a number representing the maximum number of sample stores that can be used to project market conditions onto a non-sample store. The minimum number sample stores parameter may contain a value for a desired minimum number of sample stores that should be used to project a non-sample store. The maximum distance between stores parameter indicates the maximum distance (e.g. number of miles) that a sample store can be from a subject non-sample store, so that the sample store's market data can be used to project the non-sample store market data or conditions. The maximum distance between stores parameter may not be enforced if a minimum number of sample stores cannot be found to project to a non-sample store. The maximum distance between stores parameter may be defined by channel and stored in a production parameter library. A static weekly copy of this library may be archived (e.g., saved for two years). System 1000 may save the product outlet identifier and the miles apart value for each sample store that was found and saved to calculate weights. System 1000 may save the average total prescriptions from the sample store factor data for every product level that the sample store and non-sample store have in common.

System 1000 may ignore a product level if a sample store has a product level that is not present or available in the non-sample store. System 1000 may assign total prescriptions equal to zero for a product level if a non-sample store has a product level that is not in the sample store. System 1000 may save the following data: non-sample product outlet identifier; channel; store type; product level; average total prescriptions for non-sample store for product level; sample store product outlet identifier; miles apart; and average total prescriptions for sample store for product level. Table C shows an example of the saved data

| Non-Sample CMF Outlet # | Channel | Store Type | Product Level | Average TRx | Sample CMF Outlet # | Miles Apart | Average TRx at Sample store for product level |
|---|---|---|---|---|---|---|---|
| 87654321 | R | F | Store | 2000 | 12345678 | 20 | 1000 |
|  |  |  | USC1 | 320 |  |  | 20 |
|  |  |  | USC2 | 100 |  |  | 0 |
|  |  |  | USC3 | 90 |  |  | 10 |

-continued

| Non-Sample CMF Outlet # | Channel | Store Type | Product Level | Average TRx | Sample CMF Outlet # | Miles Apart | Average TRx at Sample store for product level |
|---|---|---|---|---|---|---|---|
|  |  |  | USC4 | 80 |  |  | 10 |
|  |  |  | USC5 | 70 |  |  | 10 |
|  |  |  | CMF7 | 10 |  |  | 5 |

The channel criteria in the store distance evaluation process may be used to select stores that are added to the multi-channel store distance file for a given product outlet. The channel of the non-sample store may determine which stores will be selected as the sample stores within the store distance evaluation process. A weight of zero may be assigned for a product level within a non-sample store, if the product level is not present in the sample store that is being used to project market conditions to the non-sample store.

At step 6050, system 1000 may calculate a weight for each product level that the subject non-sample store and the sample store have in common for each non-sample store found and saved. The following exemplary equation may be used to calculate the weight for each product level:

$$Wi=((1/di^{}p)/(S(i=1 \text{ to } n)ti/di^{}p))^{*}tu, \quad (4)$$

where $Wi$=weight applied to the sample store data, $di$=distance from non-sample to sample store; (in relative distance sequence, where 1 is the closest); $ti$=store size in Total prescriptions Volume of the sample store; $tu$=store size in Total prescriptions Volume of the non-sample store, $p$=a variable parameter, $n$=the number of sample stores, and $S$=sum.

A weight cap parameter may indicate the maximum weight a sample store can be assigned for a particular product level. The weight cap parameter may be defined by channel and stored in a production parameter library. As previously noted, a weekly copy of the production parameter library may regularly stored in an archive (e.g., saved for 2 years). System 1000 may limit the weight assigned to a sample store when the normally computed weight (e.g., by equation 4) exceeds maximum weight cap.

System 1000 may save the values of both the normally computed and limited weights assigned to a sample store. System 1000 may also save the following data: non-sample product outlet identifier; channel; store type; product level; average total prescriptions for non-sample store for product level; sample store product outlet identifier; miles apart; average total prescriptions for sample store for product level; weight assigned to sample store before capping; and weight assigned to sample store after capping. Table D shows an example of the saved data.

TABLE D

| Non-Sample CMF Outlet # | Channel | Store Type | Product Level | Average TRx | Sample CMF Outlet # | Miles Apart | Average TRx at Sample Store for product level | Weight assigned to Sample Store before capping | Weight assigned to Sample Store before capping |
|---|---|---|---|---|---|---|---|---|---|
| 87654321 | R | F | Store | 2000 | 12345678 | 20 | 1000 | 6 | 5 |
|  |  |  | USC1 | 320 |  |  | 20 |  |  |
|  |  |  | USC2 | 100 |  |  | 0 |  |  |
|  |  |  | USC3 | 90 |  |  | 10 |  |  |

TABLE D-continued

| Non-Sample CMF Outlet # | Channel | Store Type | Product Level | Average TRx | Sample CMF Outlet # | Miles Apart | Average TRx at Sample Store for product level | Weight assigned to Sample Store before capping | Weight assigned to Sample Store before capping |
|---|---|---|---|---|---|---|---|---|---|
| | | | USC4 | 80 | | | 10 | | |
| | | | USC5 | 70 | | | 10 | | |
| | | | CMF7 | 10 | | | 5 | | |

Next at step 6060, system 1000 may add non-sample store weights to generate sample store factors.

Figure 5:
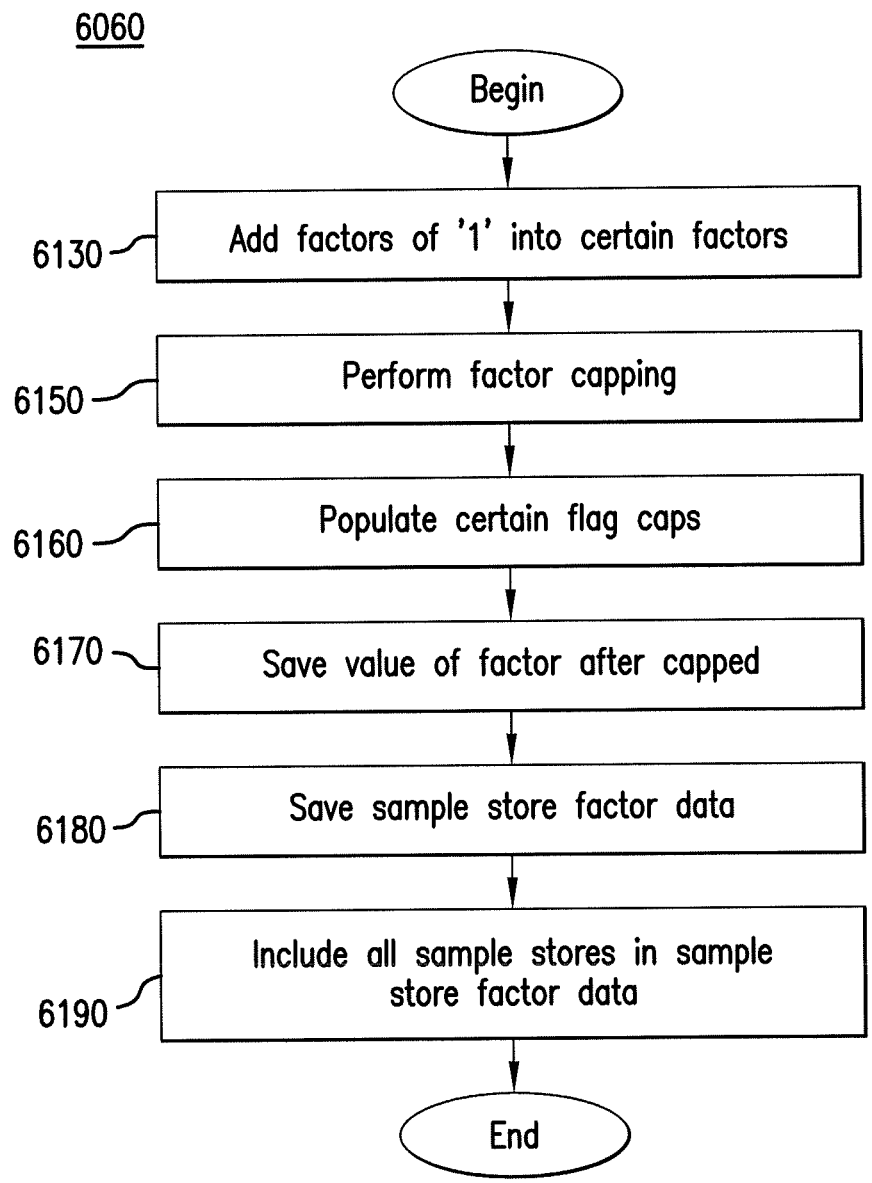
FIG. 5 is a flow diagram illustrating the steps of another exemplary process for calculating a projection factor for predicting market demand in accordance with the principles of the present invention.

FIG. 5 shows further details of a process 5000 involved at step 6060 to create sample store factors. At step 6110 in process 5000, the following factors are saved for each sample store: chain, independent, food, mass merchandise (MM), long term care (LTC) and mail order (MO). At step 6120, system 1000 may add a weight for each non-sample store product level to the appropriate factor for the sample store product level. System 1000 may add the weight to a particular factor as a function, for example, of channel and store type of the non-sample store. The functions relating channel and store types to particular factors may be defined, for example, as:

a) Retail channel and food store type: add weight to food factor.
b) Retail channel and chain store type: add weight to chain factor.
c) Retail channel and independent store type: add weight to independent factor.
d) LTC channel: add weight to LTC factor.
e) MO channel: add weight to MO factor.
f) Retail channel and MM store type: add weight to MM factor.

At step 6130, system 1000 may assign or add a value of "1" to the factor corresponding to the store type for a retail store, the LTC factor for a LTC store, or to the MO factor for a MO store. A value of "1" may be added or assigned to all product levels for the product outlet.

At step 6150, system 1000 may perform a one-time factor capping process after all the factors have been computed. When capping a LTC or MO factor, system 1000 may change or reset the final computed factor to a maximum value if the final computed factor exceeds a designated value stored in a factor cap parameter file. A factor for a sample store may be set to the designated factor cap value less one. All other factors may be set to the factor cap value. For capping a retail factor, the system may add the values in the chain, MM, independent and food factors. If the sum of these values exceeds the value in the factor cap parameter, then the equation below may be used to adjust the chain, MM, independent and food factors.

$$\text{adjusted factor} = \text{current factor} \times (A/(\text{chain factor} + MM \text{ factor} + \text{independent factor} + \text{food factor})), \quad (6)$$

where $A = (\text{factor cap value} - 1)$ if the sample store is retail, or $A = \text{factor cap value}$ if the sample store is mail order (MO) or long term care (LTC).

A factor cap parameter may have a value for the maximum factor a sample store can be assigned for a product level. This parameter may be defined by channel and may be stored in a production parameter library. A static weekly copy of the factor cap parameter values may be saved for 6 years.

At step 6160 system 1000 may populate a LTC cap flag when a LTC factor is capped, a Retail cap flag when a retail factor is capped and a MO cap flag when a MO factor is capped, etc.

At step 6170, system 1000 may save the values of the computed and capped factors. However, values of the factors prior to capping may not be saved. Further at step 6180, system 1000 may save the following data: sample product outlet identifier; channel; store type; product level; average total prescriptions; chain factor; MM factor; Ind factor; food factor; LTC factor; MO factor; retail factor cap flag; LTC factor cap flag; and MO factor cap flag. Table E shows an example of the saved data.

TABLE E

| Sample CMF Outlet # | Channel | Store Type | Product Level | Average TRx | Chain factor | MM factor | Ind factor | Food factor | LTC factor | MO Factor | Retail factor cap factor, etc |
|---|---|---|---|---|---|---|---|---|---|---|---|
| 12345678 | R | I | Store | 2000 | | | 1 | 5 | | | |
| | | | USC1 | 320 | | | 1 | 4 | | | |
| | | | USC2 | 100 | | | 1 | 6 | | | |
| | | | USC3 | 90 | | | 1 | 1.5 | | | |
| | | | USC4 | 80 | | | 1 | 4 | | | |
| | | | USC5 | 70 | | | 1 | 2 | | | |
| | | | CMF7 | 10 | | | 1 | 6 | | | |

At step 6190, system may include all sample stores in the sample store factor data. When a sample store is not used to project a non-sample store market conditions or data, all product levels for the sample store may have a factor of one (1) for the factor corresponding to the sample store's channel and store type. A sample store is not be used to project non-sample stores market conditions or data when it is in the excluded stores from projections parameter file or when if it was not selected during a "find sample stores" process (i.e., an elementary business process (EBP)).

Figure 6:
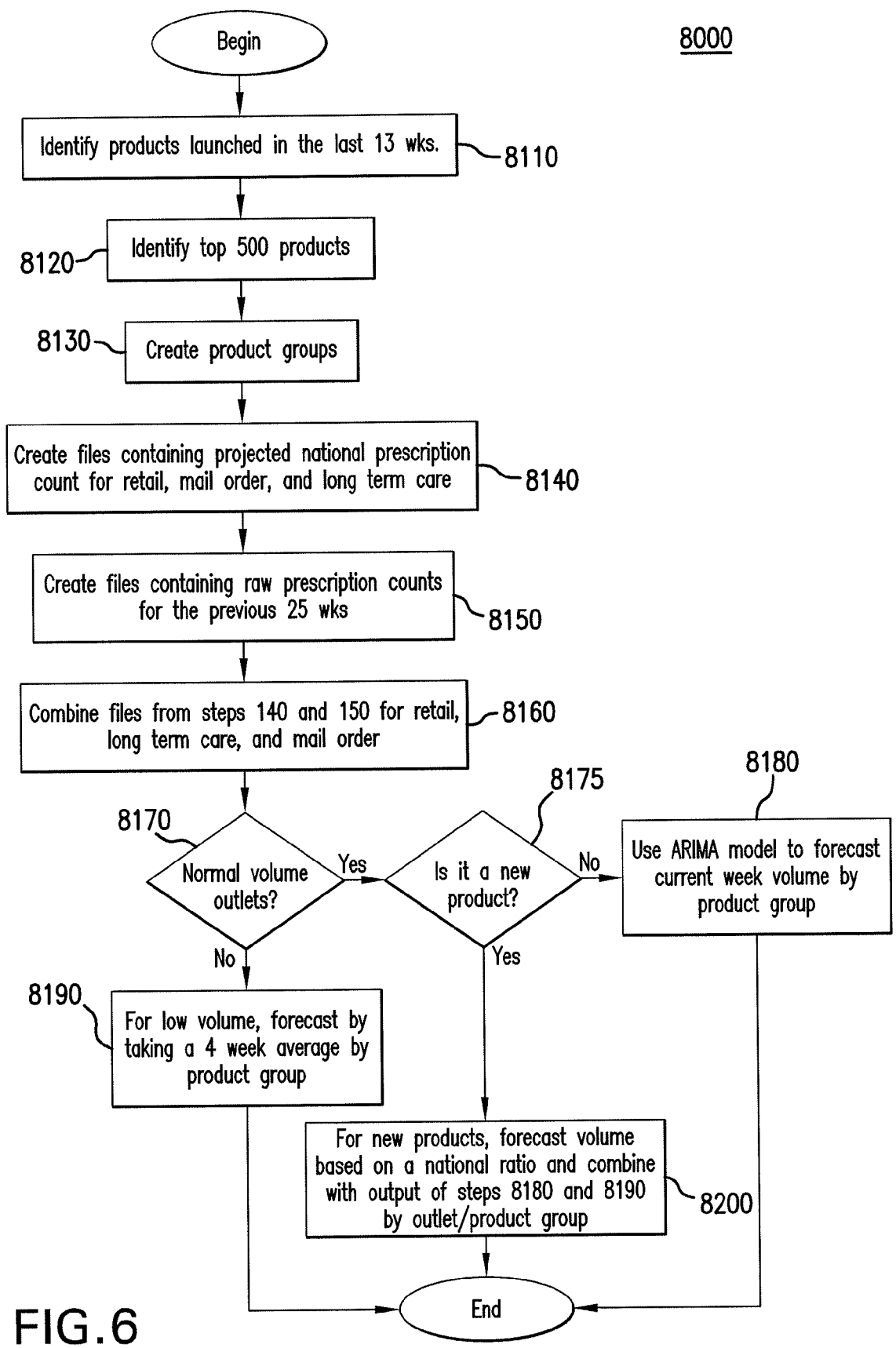
FIG. 6 is a flow diagram illustrating the steps of yet another exemplary process for calculating a projection factor for predicting market demand in accordance with the principles of the present invention.

FIG. 6 is a flow diagram of an exemplary forecasting procedure 8000 using system 1000 that may be utilized for predicting market conditions, data or statistics. At step 8110 in procedure 8000, system 1000 may identify products that have been launched, for example, in the last 13 weeks, based on analysis of prescription information stored in database 1030. At step 8120, system 1000 may identify top or leading products (e.g., top 500 products) based on analysis of national prescription counts information (e.g., based on prescription volume). At step 8130, system 1000 may create product groups by grouping all non-top 500 products by a therapy class and may treat the top 500 products as its own group.

Next at step 8140, system 1000 may generate data files containing projected national prescription count information (e.g., national prescription audit or NPA information) by product for each of three channels (namely retail, mail order, and long term care). The files may include may include, for example, 25 weeks of information from history, and also an estimate of national current week volume from an early insight database. The files may be grouped by product groups.

At step 8150, system 1000 generates data files containing raw prescription counts at the outlet/product level for the previous 25 weeks. These files also may be grouped by product groups. At step 8160, system 1000 may combine files generated at steps 8140 and steps 8150 for the retail, long term care, and mail order channels. Outlet/product data may be separated or classified into two groups, for example, normal and low volume groups. Average prescriptions per week, number of missing weeks, and maximum prescriptions per week data may be used to determine how a particular outlet/product data is classified. At step 8170 system 1000 determines outlet/product data corresponds to a normal or low volume group classifications and at step 8180 determines whether a new product is involved. At step 8190, for low volume outlets data involving new or old products, system 1000 may forecast the current week volume by taking a four-week average of outlet/product raw prescription counts. Conversely, for normal volume outlets data that does not involve a new product, at step 8180 system 1000 may use a suitable model (e.g., Autoregressive Integrated Moving Average (ARIMA) model) to forecast the current week volume based on outlet/product raw prescription counts for the past 25 weeks and projected national prescription counts for both the current week and the past 25 weeks. Further, for normal volume outlets data that does involve a new product, at step 8200 system 1000 may forecast a new product volume based on a national ratio of product to therapy class prescription counts applied to the outlet level therapy class prescription counts. System 1000 may combine the forecasts generated at steps 8180, 8190 and 8200, to generate a final forecast.

Figure 7A:
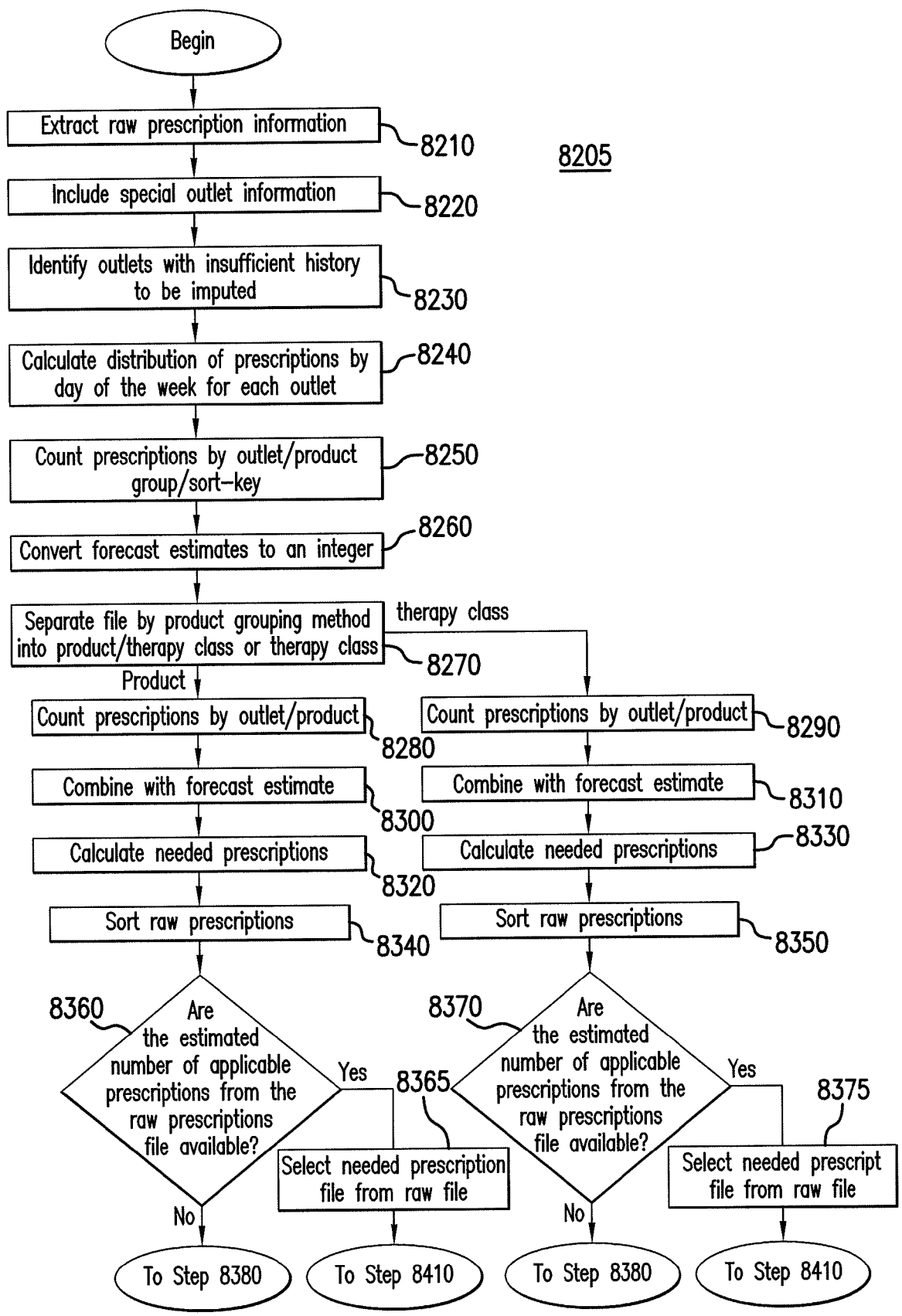
FIG. 7 is a flow diagram illustrating the steps of an exemplary process for calculating data adjustment factors for reconciling imputed and actual demand for reporting outlets for predicting market demand in accordance with the principles of the present invention.
Figure 7B:
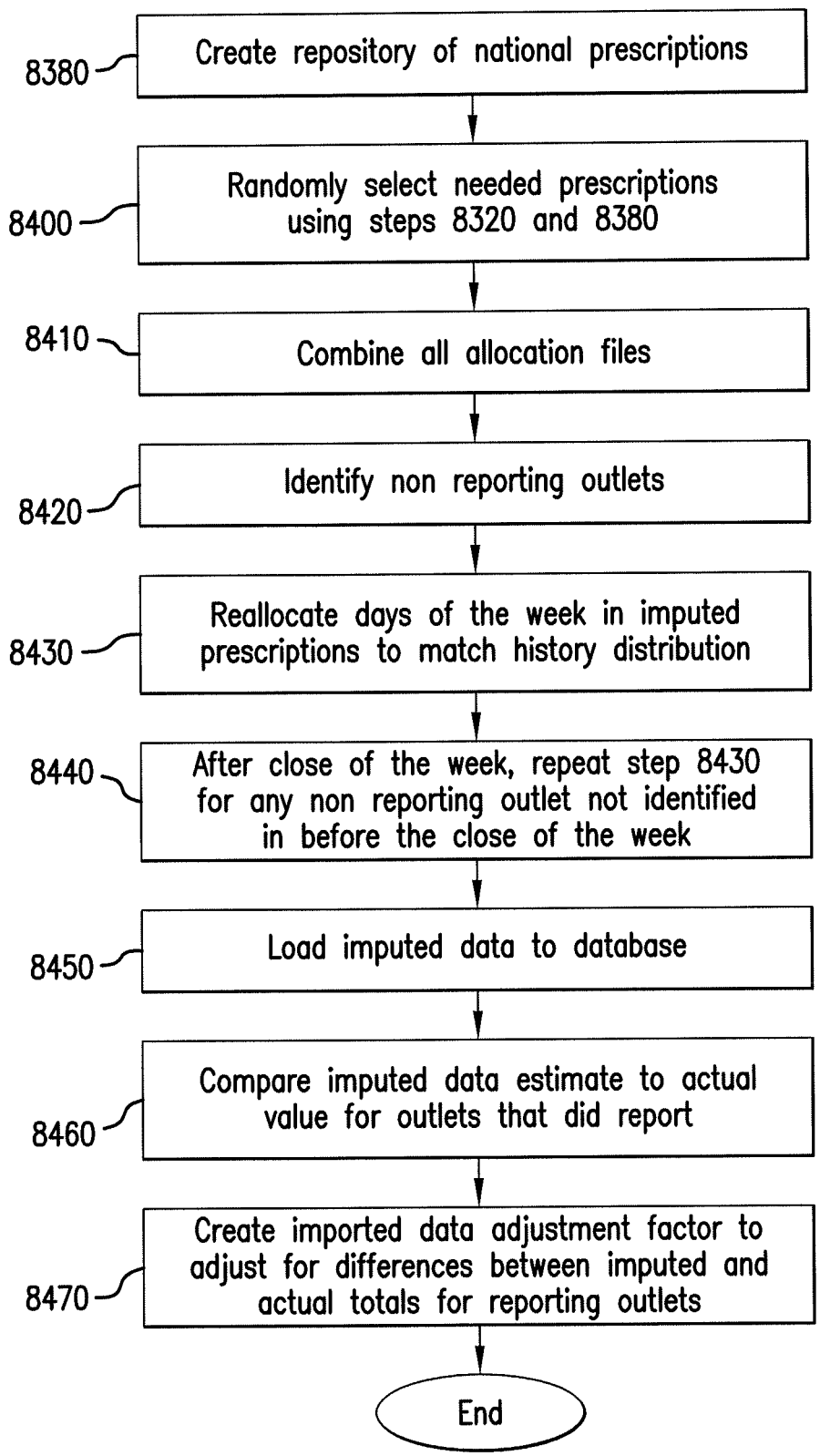

FIG. 7 shows steps 8210-8470 that may be performed by system 1000 in an exemplary imputation procedure 8205 that may be used to allocate prescriptions, product or prescriptions data to non-reporting outlets or entities (e.g. physicians) in the store universe. At step 8210, system 1000 may extract raw prescription information (e.g., from database 1030). System 1000 may then at step 8220 pull in special outlet information, and accordingly at step 8230 identify outlets with insufficient history to be imputed. The outlets with insufficient history may be excluded from further processing. Next at step 8240, system 1000 may calculate the distribution of prescriptions by day of the week for each outlet. This distribution may be adjusted for a holiday week based on a holiday proportion file. System 1000 may then at step 8250 count prescriptions by outlet/product group/sort_key (numerator), and separate data into various files for future processing. At step 8260, each forecast estimate in a final forecast file (e.g., from process 8200 FIG. 6) is converted to an integer value. At step 8270, system 1000 may further separate the files by a product grouping method (e.g. product/therapy class or therapy class)

System 1000 may perform subsequent processing steps 8280, 8300, 8320, 8340, 8360, 8365 and 8380 on the separated files for each grouping (i.e., product/therapy class and therapy class). At step 8280, system 1000 may count prescriptions by outlet/product. At step 8300, these counts may be combined with the forecast estimate. If there is a forecast estimate but no prescription counts, then the data may be placed a separate output file. At step 8320 system 1000 may calculate the needed raw prescriptions counts by imputation (e.g. as forecast*numerator/denominator). At step 8340, system 1000 may sort the raw prescriptions counts by outlet/therapy class/sort key and random number. At step 8360, system 1000 may determine whether the estimated number of applicable prescriptions from the raw prescriptions file is available. If estimated number of applicable prescriptions is available, system 1000 may at step 8365 randomly select the needed prescriptions from the raw prescriptions file. Step 8365 may be repeated twice if necessary. If this is not sufficient, the remaining number of prescriptions needed may be output to a separate file.

If the estimated number of applicable prescriptions from the raw prescriptions file are not available, system 1000 may at step 8380 access or generate a repository of national prescriptions by product file. Where more prescriptions are needed for imputation than are available in that outlet's history, the prescriptions may be selected from the pool of all national prescriptions. At step 8400, the needed prescriptions may then be randomly selected (e.g., using steps 8320 and 8330) from the national pool of prescriptions.

After a sufficient number of needed prescriptions have been generated, system 1000 at step 8410 may combine all allocation files. Before the close of week, at step 8420 system 1000 may identify non-reporting outlets, which become eligible for use of imputed prescriptions. At step 8430 system 1000 may reallocate days of the week in the imputed prescriptions to match history distribution. After the close of week, system 1000 may repeat step 8430 for any non-reporting outlet that was not identified as such before the close of week (step 8440). Next, at step 8450 system 1000 may load imputed prescriptions data to a database (e.g., database 1030), and at step 8460 may compare imputed data estimates to actual values for outlets that did report prescriptions data. Further, at step 8470, system 1000 may generate an imputed data adjustment factor to adjust for any difference between imputed total and actual totals for reporting outlets.

In the context of weekly forecasting of market conditions based on prescriptions/scripts data or other data, it will be understood that "trailing" data is old data received in the current week, in other words the data represents a prescription with a dispense date that is older then the current cycle week. Trailing data may be received on a regular basis from stores and suppliers. The trailing data may be expected to show repeatable trends similar to the other store monitoring evaluations. A trailing data factor reflects the trend of the trailing data.

Back data is similar to trailing data in that the scripts are for an older week than is currently being processed. Scripts data may be labeled as back data when the trailing data is unusual or exceeds some threshold parameter. To avoid breaking or disrupting trends, back data may not be used in current or future trailing data factor calculations.

In the operation of system 1000, all of the trailing data parameters are stored in the databases and processing files a manner similar to other statistical parameters. The trailing data parameters are defined at the global level; however, supplier and store overrides of the global settings are possible. If the supplier or store level override parameters exist and are available, they are used for data processing in favor of the global parameters.

A trailing data factor for a particular outlet may be calculated based on the average of the prior weeks of trailing data (e.g., six weeks). The trailing data for a supplier/store is added into the daily data and trailing data of the data week for which it belongs. The trailing data does not affect any already-existing processing status code (e.g., the data will not be reevaluated). If there is no data for a particular data week for the particular supplier/store, then default processing status code may be blank.

Figure 8:
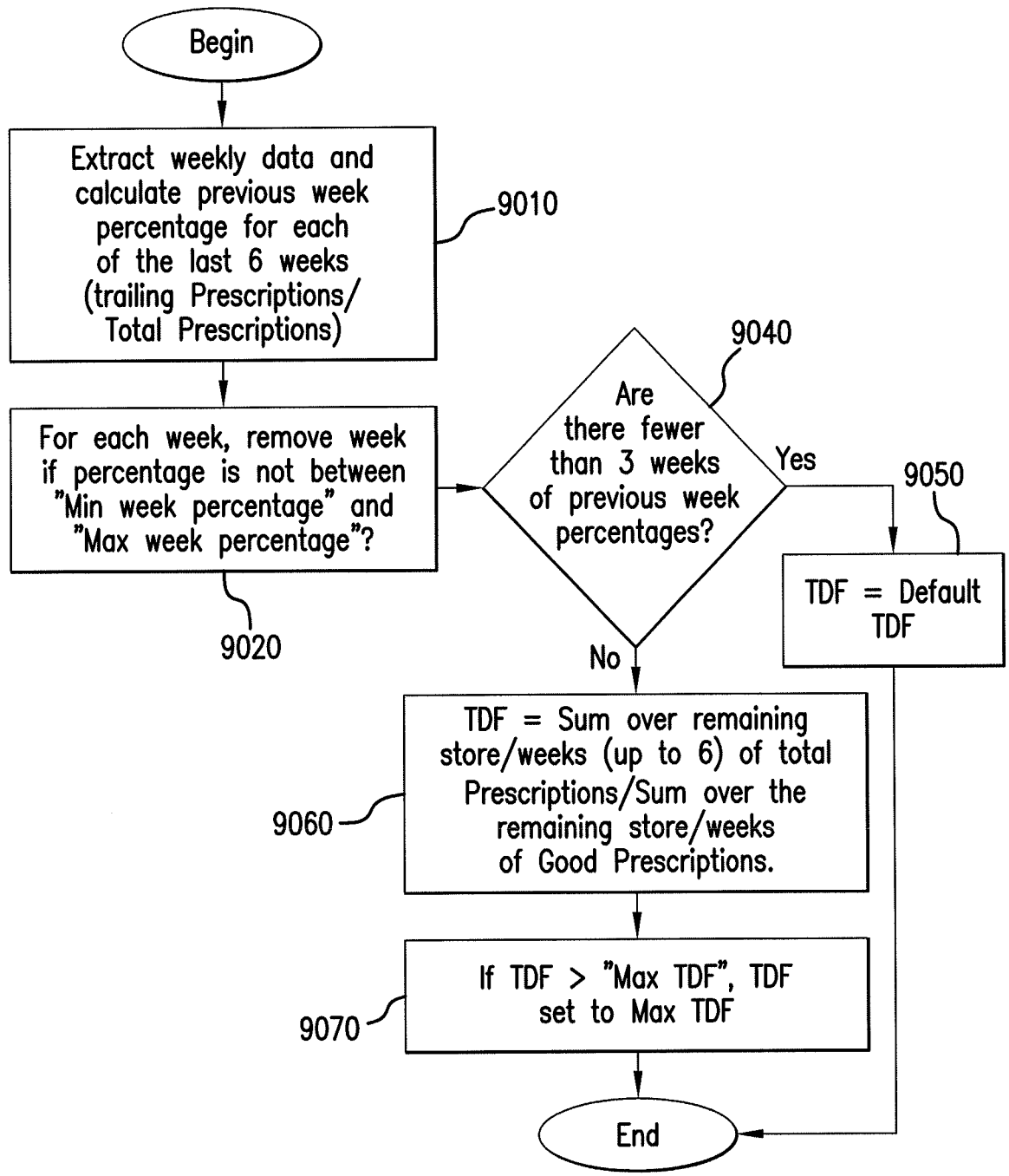
FIG. 8 is a flow diagram illustrating an exemplary process whereby market information is predicted in accordance with the principles of the present invention.

FIG. 8 illustrates an exemplary procedure 9000 for calculating a trailing data factor (TDF) by store (i.e., how much of the data is trailing) using the system 1000. For purposes of the trailing data factor calculation in procedure 9000, the total prescriptions are given by the following equation:

$$\text{total prescriptions} = \text{sum of good prescriptions and trailing prescriptions} \quad (10)$$

The trailing data calculations (e.g. procedure 9000) may require that suitable initialization parameters and limits are defined. The initialization parameters and limits may, for example, include terms such as "Default TDF", "Max TDF", "Min Week Percentage", "Max Week Percentage Back Data Max %", "Min Weeks for TDF", and "TDF Weeks", which are defined as follows:

Default TDF: if after preprocessing the Trailing data history file a Store has two or fewer weeks in the file, the system may set trailing data factor to the default. The initial value should be 1.

Max TDF: if the TDF>Max TDF, the system should set TDF to Max TDF. The Max TDF initial value should be 1.5.

Min Week Percentage: During evaluation of history, if the calculated percentage between Good Prescription and Total Prescriptions for a week is less then Min Week Percentage, the week should not be used as part of the TDF calculation. The Min TDF initial value should be 1.

Max Week Percentage Back Data Max %: during evaluation of history, if the calculated percentage between Good Prescriptions and Total Prescriptions for a week is greater then Max Week Percentage, the week should not be used as part of the TDF calculation. The Max TDF initial value should be 1.5.

Min Weeks for TDF: the minimum number of weeks required to calculate the TDF. If less than the minimum, then the system should use the default TDF. The initial value should be 3.

TDF Weeks: the number of weeks to examine for TDF calculations. The initial value should be 6.

The following data fields from the history file may be required for trailing data calculations and storing results: 1) store (trailing data is calculated for each store); 2) week data received (week trailing data factor is calculated); 3) total prescriptions (current week good prescriptions (dispense date week same as data receipt)); 4) trailing prescriptions (current week trailing prescriptions (dispense date in earlier week then receipt date)); 5) total good prescriptions (calculated) (sum of total prescriptions and trailing prescriptions); 6) trailing data factor (trailing data factor percentage is calculated from total prescriptions and good prescriptions); and 7) back data indicator (value indicating whether or not the trailing data is really back data and not part of a normal trend).

With renewed reference to FIG. 8, in procedure 9000, at step 9010 system 1000 may extract weekly data and calculate a previous week percentage for each of the last 6 weeks. The previous week percentage is equal to trailing prescriptions/total prescriptions at the same level. At step 9020 system 1000 may determine whether the previous week percentage is between a minimum week percentage and the maximum week percentage. If the previous week percentage is not within the minimum and maximum limits, system 1000 may set a back data flag, and further at step 9040 determine whether there are fewer than three weeks of acceptable previous week percentages. If there are fewer than three weeks of acceptable previous week percentages, then at step 9050 system 1000 may set the trailing data factor to default trailing data factor. Conversely, when more than three weeks of acceptable previous week percentages are present system 1000 at step 9060 may set the TDF equal to the ratio of the sum over remaining store/weeks (up to 6) of total prescriptions to the sum over remaining store/weeks of good prescriptions. If the TDF exceeds a maximum allowed value "Max TDF", then the TDF may be set to Max TDF (step 9070).

It will be appreciated by those skilled in the art that the methods of FIGS. 1-8 can be implemented on various standard computer platforms operating under the control of suitable software defined by FIGS. 1-8. In some cases, dedicated computer hardware, such as a peripheral card in a conventional personal computer, can enhance the operational efficiency of the above methods.

Figure 9:
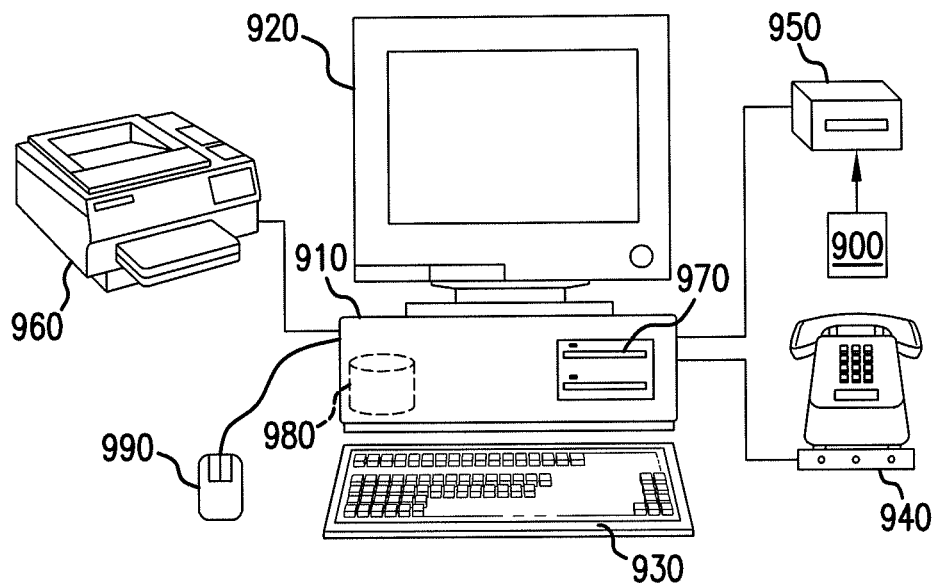
FIG. 9 is a schematic illustration of an exemplary computer system that is configured for performing the processes of FIGS. 2-8, in accordance with the principles of the present invention.
Figure 10:
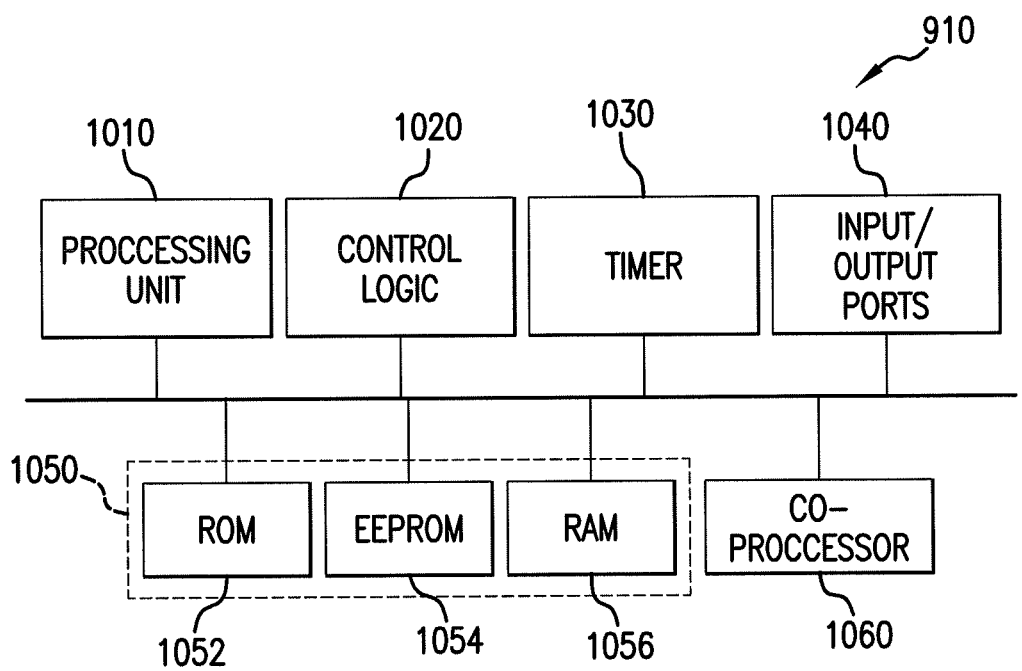
FIG. 10 is a block diagram illustrating a processing section of the computer system of FIG. 9, in accordance with the principles of the present invention.

FIGS. 9 and 10 show exemplary computer hardware arrangements suitable for performing the methods of the present invention. Referring to FIG. 9, the computer arrangement includes a processing section 910, a display 920, a keyboard 930, and a communications peripheral device 940 such as a modem. The computer arrangement may include a digital pointer 990 such as a "mouse." The computer arrangement also may include other input devices such as a card reader 950 for reading an account card 900. In addition, the computer arrangement may include output devices such as a printer 960. The computer hardware arrangement may include a hard disk drive 980 and one or more additional disk drives 970 that can read and write to computer readable media such as magnetic media (e.g., diskettes or removable hard disks), or optical media (e.g., CD-ROMS or DVDs). Disk drives 970 and 980 may be used for storing data and application software.

FIG. 10 shows an exemplary functional block diagram of processing section 910 in the computer arrangement of FIG. 9. Processing section 910 includes a processing unit 1010, a control logic 1020, and a memory unit 1050. Processing section 910 may also include a timer 1030 and input/output ports 1040. Processing section 910 may further include an optional co-processor 1060, which is suitably matched to a microprocessor deployed in processing unit 1010. Control logic 1020 provides, in conjunction with processing unit 1010, controls necessary to handle communications between memory unit 1050 and input/output ports 1040. Timer 1030 may provide a timing reference signal for processing unit 1010 and control logic 1020. Co-processor 1060 enhances system abilities to perform complex computations in real time, such as those required by cryptographic algorithms. Memory unit 1050 may include different types of memory, such as volatile and non-volatile memory and read-only and programmable memory. Memory unit 1050 may, for example, include read-only memory (ROM) 1052, electrically erasable programmable read-only memory (EEPROM) 1054, and random-access memory (RAM) 1056. Various computer processors, memory configurations, data structures and the like can be used to practice the present invention, and the invention is not limited to a specific platform.

In accordance with the present invention, software (i.e., instructions) for implementing the aforementioned demand forecasting systems and methods (algorithms) can be provided on computer-readable media. It will be appreciated that each of the steps (described above in accordance with this invention), and any combination of these steps, can be implemented by computer program instructions. These computer program instructions can be loaded onto a computer or other programmable apparatus to produce a machine such that the instructions, which execute on the computer or other programmable apparatus, create means for implementing the functions of the aforementioned demand forecasting systems and methods. These computer program instructions can also be stored in a computer-readable memory that can direct a computer or other programmable apparatus to function in a particular manner such that the instructions stored in the computer-readable memory produce an article of manufacture including instruction means, which implement the functions of the aforementioned demand forecasting systems and methods. The computer program instructions can also be loaded onto a computer or other programmable apparatus to cause a series of operational steps to be performed on the computer or other programmable apparatus to produce a computer implemented process such that the instructions which execute on the computer or other programmable apparatus provide steps for implementing the functions of the aforementioned demand forecasting systems and methods. It will also be understood that the computer-readable media on which instructions for implementing the aforementioned demand forecasting systems and methods are be provided include, without limitation, firmware, microcontrollers, microprocessors, integrated circuits, ASICS, and other available media.

It will be understood, further, that the foregoing is only illustrative of the principles of the invention, and that those skilled in the art can make various modifications without departing from the scope and spirit of the invention, which is limited only by the claims that follow.

The invention claimed is:

1. A method comprising:
   receiving historical market data for one or more sample outlets;
   generating a first preliminary forecast of a product demand for a first time interval, wherein generating the first preliminary forecast comprises:
      generating a sample forecast for at least one sample outlet of the one or more sample outlets based on the historical market data, and
      for at least one non-sample outlet determining a projection factor and estimating a non-sample forecast using the projection factor;
   receiving a first live market data during the first time interval;
   screening the first live market data to exclude from subsequent processing a portion of the first live market data corresponding to one or more unusual events;
   determining, by one or more processing devices, a first adjustment factor based on a difference between the screened live market data, which excludes the portion of the first live market data corresponding to one or more unusual events, and the first preliminary forecast; and
   updating the first preliminary forecast for the first time interval using the first adjustment factor to derive a second preliminary forecast for the first time interval.

2. The method of claim 1, further comprising:
   receiving a second live market data for a second time interval;
   screening the second live market data to eliminate data corresponding to one or more unusual events;
   calculating a second adjustment factor based on a difference between the second live market data and the second preliminary forecast; and
   updating the second preliminary forecast using the second adjustment factor.

3. The method of claim 1, wherein calculating the first adjustment factor includes determining a trailing data factor.

4. The method of claim 1, wherein the first adjustment factor is calculated on a product-level.

5. The method of claim 1, wherein the first live market data indicates data gathered during a time interval that overlaps with the first time interval for the first preliminary forecast.

6. A computer-readable non-transitory storage medium encoded with a computer program, the program comprising instructions that when executed by one or more processors cause the one or more processors to perform operations comprising:
   receiving historical market data for one or more sample outlets;
   generating a first preliminary forecast of a product demand for a first time interval, wherein generating the first preliminary forecast comprises:
      generating a sample forecast for at least one sample outlet of the one or more sample outlets based on the historical market data, and
      for at least one non-sample outlet, determining a projection factor and generating a non-sample forecast using the projection factor;
   receiving a first live market data during the first time interval;
   screening the first live market data to exclude, from subsequent processing, a portion of the first live market data corresponding to one or more unusual events;
   calculating a first adjustment factor based on a difference between the screened live market data, which excludes the portion of the first live market data corresponding to one or more unusual events, and the first preliminary forecast; and
   updating the first preliminary forecast for the first time interval using the first adjustment factor to derive a second preliminary forecast for the first time interval.

7. The computer-readable medium of claim 6, further comprising instructions operable to direct the processing unit to perform:
   receiving a second live market data for a second time interval;
   screening the second live market data to eliminate data corresponding to one or more unusual events;
   calculating a second adjustment factor based on a difference between the second live market data and the second preliminary forecast; and
   updating the second preliminary forecast using the second adjustment factor.

8. The computer-readable medium of claim 6, wherein calculating the first adjustment factor includes determining a trailing data factor.

9. The computer-readable medium of claim 6, wherein the first adjustment factor is calculated on a product-level.

10. The computer-readable medium of claim 6, wherein the first live market data indicates data gathered during a time interval that overlaps with the first time interval for the first preliminary forecast.

11. A system comprising:
one or more processing devices; and
a non-transitory computer-readable medium coupled to the one or more processing devices having instructions stored thereon which, when executed by the one or more processing devices, cause the one or more processing devices to perform operations comprising:
receiving historical market data for one or more sample outlets;
generating a first preliminary forecast of a product demand for a first time interval, wherein generating the first preliminary forecast comprises:
generating a sample forecast for at least one sample outlet of the one or more sample outlets based on the historical market data, and
for at least one non-sample outlet, determining a projection factor and generating a non-sample forecast using the projection factor;
receiving a first live market data during the first time interval;
screening the first live market data to exclude, from subsequent processing, a portion of the first live market data corresponding to one or more unusual events;
determining a first adjustment factor based on a difference between the screened live market data, which excludes the portion of the first live market data corresponding to one or more unusual events, and the first preliminary forecast; and
updating the first preliminary forecast for the first time interval using the first adjustment factor to derive a second preliminary forecast for the first time interval.

12. The system of claim 11, wherein the processing arrangement is configured to further perform:
receiving a second live market data for a second time interval;
screening the second live market data to eliminate data corresponding to one or more unusual events;
calculating a second adjustment factor based on a difference between the second live market data and the second preliminary forecast; and
updating the second preliminary forecast using the second adjustment factor.

13. The system of claim 11, wherein calculating the first adjustment factor includes determining a trailing data factor.

14. The system of claim 11, wherein the first adjustment factor is calculated on a product-level.

15. The system of claim 11, wherein the first live market data indicates data gathered during a time interval that overlaps with the first time interval for the first preliminary forecast.

16. The method of claim 1, wherein determining a first adjustment factor based on a difference between the screened live market data, which excludes the portion of the first live market data corresponding to one or more unusual events, and the preliminary forecast comprises:
calculating a first adjustment factor based on a difference between the screened live market data, which excludes the portion of the first live market data corresponding to one or more unusual events, and the sample forecast that was generated for at least one sample outlet of the one or more sample outlets.

* * * * *